(12) United States Patent
Eijgendaal et al.

(10) Patent No.: US 7,423,040 B2
(45) Date of Patent: *Sep. 9, 2008

(54) STABLE CRYSTALLINE FORM OF BIFEPRUNOX MESYLATE, DOSAGE FORMS THEREOF AND METHODS FOR USING SAME

(76) Inventors: Irene Eijgendaal, c/o C. J. van Houtenlaan 36, 1381 CP Weesp (NL); Gerrit Klein, c/o C. J. van Houtenlaan 36, 1381 CP Weesp (NL); Maria J. L. Terhorst-Van Amstel, c/o C. J. van Houtenlaan 36, 1381 CP Weesp (NL); Klaas Zwier, c/o C. J. van Houtenlaan 36, 1381 CP Weesp (NL); Nico Bruins, c/o C. J. van Houtenlaan 36, 1381 CP Weesp (NL); Hendrikus T. Rigter, c/o C. J. van Houtenlaan 36, 1381 CP Weesp (NL); Erik Gout, c/o C. J. van Houtenlaan 36, 1381 CP Weesp (NL); Caroline Boon, c/o C. J. van Houtenlaan 36, 1381 CP Weesp (NL); Michiel H. De Vries, c/o C. J. van Houtenlaan 36, 1381 CP Weesp (NL)

( * ) Notice: Subject to any disclaimer, the term of this patent is extended or adjusted under 35 U.S.C. 154(b) by 133 days.

This patent is subject to a terminal disclaimer.

(21) Appl. No.: 11/354,652

(22) Filed: Feb. 16, 2006

(65) Prior Publication Data

US 2006/0194812 A1 Aug. 31, 2006

Related U.S. Application Data

(60) Provisional application No. 60/654,149, filed on Feb. 18, 2005.

(51) Int. Cl.
*A61K 31/501* (2006.01)
*C07D 413/06* (2006.01)
(52) U.S. Cl. .................. 514/254.02; 544/368
(58) Field of Classification Search ............ 514/254.02; 544/368
See application file for complete search history.

(56) References Cited

U.S. PATENT DOCUMENTS

2004/0077631 A1 4/2004 Van Aar et al.
2005/0234389 A1 10/2005 Bouwstra et al.

FOREIGN PATENT DOCUMENTS

| EP | 0 908 458 A1 | 4/1999 |
|---|---|---|
| EP | 0 189 612 A1 | 8/2006 |
| WO | WO 97/36893 | 10/1997 |
| WO | WO 00/29397 | 5/2000 |
| WO | WO 01/74365 | 10/2001 |
| WO | WO 02/066449 A2 | 8/2002 |
| WO | WO 2006/032202 | 3/2006 |
| WO | WO 2006/087369 | 8/2006 |
| WO | WO 2007/023141 | 3/2007 |

OTHER PUBLICATIONS

U.S. Appl. No. 11/727,173, filed Mar. 2007, Eijgendaal et al.*
Robichaud et al., Annual Reports In Medicinal Chemistry, Recent Advances In Selective Serotonin Receptor Modulation, pp. 11-20, 2000.*
TenBrink et al., Annual Reports In Medicinal Chemistry, Recent Advances In Dopamine D3 and D4 Receptor Ligands and Pharmacology, pp. 43-51, 1994.*
Haleblian et al., "Pharmaceutical Applications of Polymorphism," *Journal of Pharmaceutical Sciences*, 58(8):911-929 (1969).
European Search Report for EP 03 10 2573.
Co-pending U.S. Appl. No. 10/920,386, Inventors: Eijgendaal et al., filed Aug. 18, 2004.
Co-pending U.S. Appl. No. 10/920,361, Inventors: Eijgendaal et al., filed Aug. 18, 2004.
"Bifeprunox—Atypical Antipsychotic Drug," Drug Development Technology, pp. 1-3, 2007, www.drugdevelopment—technology.com/projects/bifeprunox/.
"Solvay Announces New Drug Plans for Schizophrenia," Schizophrenia Daily New Blog, pp. 1-4 (2004), www.schizophrenia.com/sznews/archives/000573.html.
(XP-001061442) Johnston, L.C. et al., "134P: The Novel Dopamine D2 Receptor Partial Agonist, SLV-308, Reverses Motor Disability in MPTO-Lesioned Common Marmosets (CALLITHRIXJACCHUS)," British Journal of Pharmacology, vol. 133, No. 2 (2001).
(XP-001061489) Feenstra, R. et al., "Antiparkinsonian Antidepressant Anxiolytic Dopamine D2 Partial Agonist 5-HT1A Agonist," Drugs of the Future, vol. 26, No. 2, 2001, pp. 128-132.
(XP-001197381) McCreary, et al., "SLV308: A Novel Antiparkinsonian Agent With Antidepressant and Anxiolytic Efficacy," Abstracts of the Society for Neuroscience (2001).
(XP-002412435) Hesselink, M. et al., "308, A Molecule Combining Potent Partial Dopamine b2 Receptor Agonism with Serotonin 5-HT1A Receptor Agonism: In vitro and in vivo neuro-chemistry," 31st Annual Meeting of the Society for Neuroscience (2001).
(XP-002412436) Johnston, L.C. et al., "SLV308: Antiparkinsonian Effects in the MPTP-Treated Common Marmoset (*Callithrix jacchus*)," 31st Annual Meeting of the Society for Neuroscience (2001).
(XP-002412438) Long Act Sustained-Relase Formulations for Treating Parkinson's Disease, Comprise a Dopamine Receptor Agonist and Biodegradable Pharmaceutical Polymer Excipient for Injection Transplant, Corresponds to WO 2006/032202.
(XP008033520) Wolf, William A., "SLV-308 Solvay," Current Opinion in Investigational Drugs, vol. 4, No. 7, 2003, pp.878-882.
Allen, et al. "A Review of Clinical and Pathophysiologic Features," Journal of Clinical Neurophysiology, vol. 18, No. 2, 2001, pp. 128-147.
Allen, et al., "Augmentation of the Restless Legs Syndrome With Carbidopa/Levedopa," Sleep, vol. 19, No. 3, 1996, pp. 205-213.

(Continued)

*Primary Examiner*—James Wilson
*Assistant Examiner*—Ebenezer Sackey
(74) *Attorney, Agent, or Firm*—Finnegan, Henderson, Farabow, Garrett & Dunner, LLP

(57) ABSTRACT

The present disclosure provides novel pharmaceutical compounds and methods for making the same, novel pharmaceutical dosage forms and methods for making the same, and methods for using said compounds and dosage forms to treat and prevent diseases and/or disorders.

30 Claims, 9 Drawing Sheets

OTHER PUBLICATIONS

Bara-Jimenez et al., "Effects of Serotonin 5-HT1A Agonist in Advanced Parkinson's Disease," Movement Disorders, vol. 20, No. 8, 2005, pp. 932-936.
Bennett, et al., "Pramipexole—A new dopamine agonist for the treatment of Parkinson's Disease," Journal of Neurological Sciences, vol. 163, 1999, pp. 25-31.
Berendsen, et al., "Selective Activation of 5HT1A Receptors Induces Lower Lip Retraction in the Rat," Pharmacology Biochemistry & Behavior, vol. 33, pp. 821-827, 1989.
Bibbiani, et al., "Serotonin 5-HT1A Agonist Improves Motor Complications In Rodent and Primate Parkinsonian Models," Neurology, vol. 57, 2001, pp. 1829-1834.
Bickel, M.H., "The Pharmacology and Biochemistry of N-Oxides," Pharmacological Reviews, vol. 21, No. 4, pp. 325-355, 1969.
Blandini, et al., "Functional Changes of the Basal Ganglia Circuitry in Parkinson's Disease," Progress in Neurobiology, vol. 62, 2000, pp. 63-88.
Chesson, et al., "Practice Parameters for the Treatment of Restless Legs Syndrome and Periodic Limb Movement Disorder," Sleep, vol. 22, No. 7, 1999, pp. 961-968.
Christoffersen, et al., "Reversal of Haloperiodol-Induced Extrapyramidal Side Effects in Cebus Monkeys by 8-Hydroxy-2-(di-n-propylamino)tetralin and Enantiomers," Neuropsychopharmacology, vol. 18, No. 5, 1998, pp. 399-402.
Costall et al., "Differential actions of typical and atypical neuroleptic agents on two behavioural effects of apomorphine in the mouse," Proceedings of the B.P.S., pp. 381-381, 1978.
Creese et al., "3H-Spiroperidol Labels Dopamine Receptors in Pituitary and Brain," European Journal of Pharmacology, 46, pp. 377-381, 1977.
Earley, et al., "Movements During Sleep: Pergolide and Carbidopa/Levedopa Treatment of the Restless Legs Syndrome and Periodic Leg Movements in Sleep in a Consecutive Series of Patients," Sleep, vol. 19, No. 10, 1996, pp. 801-810.
Feenstra, et al., "New 1-Aryl-4-(biarylmethylene) piperazines as Potential Atypical Antipsychotics Sharing Dopamine Dz-Receptor and Serotonin 5-HT1A-Receptor Affinities," Bioorganic & Medicinal Chemistry Letters, vol. 11, 2001, pp. 2345-2349.
Feenstra, et al., "New Approaches for Psychosis Treatment: Design, Synthesis and SAR of Ligands Binding to Dopamine-D2- and Serotonin 5-HT1A Receptors," Drugs of the Future, vol. 27, Suppl. A, p. 226(p. 237), XVIIth International Symposium on Medicinal Chemistry (2002).
Fleischhacker, "Clozapine: A Comparison With Other Novel Antipsychotics," J. Clin Psychiatry, vol. 60, No. 12, 1999, pp. 30-34.
Gozlan, et al., "Identification of presynaptic serotonin autoreceptors using a new ligand: 3H-PAT," Nature, vol. 305, pp. 140-142, 1983.
Hening, et al., "Dyskinesias While Awake and Periodice Movements In Sleep In Restless Legs Syndrome: Treatment with Opioids," Neurology, vol. 36, 1986, pp. 1363-1366.
Hening, et al., "The Treatment of Restless Legs Syndrome and Periodic Limb Movement Disorder," Sleep, vol. 22, No. 7, 1999, pp. 970-999.
Hesselink, M.B., et al., "P2151"'"DU127090, SLV308 and SLV318: Characterization of a Chemically Related Class of Partial Dopamine Agonists with Varying Degrees of 5-HT1A Agonism," EFNS European Journal of Neurology, vol. 10 (Suppl. 1), 2003, pp. 125-204.
Hornykiewicz, Oleh, "Dopamine (3-Hydroxytyramine) and Brain Function," Pharmaceutical Reviews, vol. 18, No. 2, 1966, pp. 925-964.
Jankovic, "Natural Course and Limitations of Levodopa Therapy," Neurology, vol. 43, No. 2, Supplement 1, 1993, pp. S1-14 thru S1-17.
Jenner, Peter, "Pharmacology of Dopamine Agonists in the Treatment of Parkinson's Disease," Neurology vol. 58 (Suppl. 1), 2002, pp. S1-S8.
Johnston, et al., P2158, "Association between Instrinsic Activity and the Antiparkinsonian Effects of a Novel Dopamine D2 Agonist series in the 1-methyl-4phenyl-1,2,3,6-tetrahydeopyridine Treated Primate Model of Parkinson's Disease," EFNS European Journal of Neurology, vol. 10 (Suppl. 1), 2003, pp. 169-170.
Jost, et al., "Efficacy and tolerability of Stalevo® in Patients with Parkinson's Disease Experiencing Wearing-off," Akt Neurol, vol. 32, Supplement 6, 2005, pp. S318-S325 (XP009074453), Abstract.
Kannari, et al., "Tandospirone Citrate, selective 5-HT1A Agonist, Alleviates L-DOPA-Induced Dyskinesia in Patients with Parkinson's Disease," BRAIN and NERVE, vol. 54, No. 2, 2002, pp. 133-137, Abstract.
Kim, et al., "Risperidone Dosing Pattern and Clinical Outcome in Psychosis: An Analysis of 1713 Cases," J. Clin Psychiatry, vol. 66, No. 7, 2005, pp. 887-893.
Lange, et al., "Terguride Stimulates Locomotor Activity at 2 Months but Not 10 Months after 1-methyl-4-phenyl-1,2,3,6-tetrahydropyridine Treatment of Common marmosets," European Journal of Pharmacology, vol. 212, 1992, pp. 247-252.
Langston, et al., "MPTP: Current Concepts and Controversies," Clinical Neuropharmacology, vol. 9, No. 6, 1986, pp. 485-507.
Langston, et al., "MPTP-induced Parkinsonism in Human and Nonhuman Primates—Clinical and Experimental Aspects," Acta Neurol Scan, vol. 70 (Suppl. 100), 1984 pp. 49-54.
Lledo, A., "Dopamine Agonists: The Treatment for Parkinson's Disease in the XXI Century?," Parkinsonism and Related Disorders, vol. 7, 2001, pp. 51-58.
Lozano, et al., "New Developments in Understanding the Etiology of Parkinson's Disease and in its Treatment," Current Opinion in Neurobiology, vol. 8, 1998, pp. 783-790.
Lundbeck, et al., "Bifeprunox Mesilate," Drugs of the Future, vol. 29, No. 9, 2004, pp. 938-939.
McCreary, et al., "SLV308: A Novel Antiparkinsonian Agent With Antidepressant and Anxiolytic Efficacy," 31st Annual Meeting of the Society for Neuroscience ABSTRACTS, vol. 27, Part 1, 2001, p. 531.
McCreary, et al., "The in vitro characterization of SLV308: A Novel Dopamine Ds/D3 partial Agonist and 5-HT1A Full Agonist for the Treatment of Parkinson's Disease," Movement Disorders, vol. 21, Suppl. 13, pp. S79-S80, 2006.
Olanow, et al., "Multicenter, Open-Label, Trial of Sarizotan in Parkinson Disease Patients With Levodopa-Induced Dyskinesias (the SPLENDID Study)," Clin Neuropharmacol, vol. 27, No. 2, 2004, pp. 58-62.
Pearce, et al., "De Novo Administration of Ropinirole and Bromocriptine Induces Less Dyskinesia Than L-Dopa in the MPTP-Treated Marmoset," Movement Disorders, vol. 13, No. 2, 1998, pp. 234-241.
Pollmächer, et al., "Periodic Leg Movements (PLM): Their Relationship to Sleep Stages," Sleep, vol. 16, No. 6, 1993, pp. 572-577.
Rascol, et al., "A Five-Year Study of The Incidence of Dyskinesia In Patients With Early Parkinson's disease Who Were Treated With Ropinirole or Levodopa," The New England Journal of Medicine, vol. 342, No. 20, 2000, pp. 1484-1491.
Robichaud et al., Annual Reports in Medicinal Chemistry, Recent Advances in Selective Serotonin Receptor Modulation, pp. 11-20 (2000).
Salomon, et al., "A Highly Sensitive Adenylate Cyclase Assay," Analytical Biochemistry, 58, pp. 541-548, 1974.
Sorbera, et al., "Treatment of Bipolar Disorder Treatment of Schizophrenia Dopamine D2 Receptor Partial Agonist 5-HT1A Receptor Agonist," Drugs of the Future, pp. 992-997, 2005, vol. 30, No. 10.
Taniguchi et al., "Clozapine Dosage and Titration," Annals of Pharmacotherapy, vol. 30, No. 7-8, 1996, p. 883.
Tenbrink et al., Annual Reports in Medicinal Chemistry, Recent Advances in Dopamine D3 and D4 Receptor Ligands and Pharmacology, pp. 43-51 (1994).
Vliet, B.J. Van, et al., "DU 127090: A Highly Potent, Atypical Dopamine Receptor Ligand—High Potency But Low Efficacy at Dopamine D2 Receptors In Vitro," P.2 Psychotic Disorders Andantipsychotics, European College of Neuropsychopharmacology, vol. 10, No. 3, 2000, p. S294.
Weiss et al., "Corticotropin-Peptide Regulation of Intracellular Cyclic AMP Production in Cortical Neurons in Primary Culture," Journal of Nurochemistry, vol. 45, No. 3, pp. 869-874, 1985.
Widmark, "Studies in the concentration of indifferent narcotics in blood and tissues," Acta Medica Scandinavica, 52, pp. 87-164, 1919.
Copending U.S. Appl. No. 11/727,173, filed Mar. 23, 2007.
Copending U.S. Appl. No. 11/743,049, filed May 1, 2007.

Copending U.S. Appl. No. 11/762,206, filed Jun. 13, 2007.
Copending U.S. Appl. No. 11/762,239, filed Jun. 13, 2007.
Copending U.S. Appl. No. 11/847,197, filed Aug. 29, 2007.

Copending U.S. Appl. No. 11/847,458, filed Aug. 30, 2007.

* cited by examiner

STABLE CRYSTALLINE FORM OF BIFEPRUNOX MESYLATE, DOSAGE FORMS THEREOF AND METHODS FOR USING SAME

This application claims the benefit of priority of U.S. Provisional Application No. 60/654,149, filed on Feb. 18, 2005, entitled "STABLE CRYSTALLINE FORM OF BIFEPRUNOX MESYLATE, DOSAGE FORMS THEREOF AND METHODS FOR USING SAME," the full content of which is incorporated herein by reference.

The present disclosure relates to stable polymorphic forms of the compound 7-[4-([1,1'-biphenyl]-3-ylmethyl)-1-piperazinyl]-2(3H)-benzoxazolone monomethanesulfonate, methods for the preparation of such polymorphic forms, pharmaceutical dosage forms comprising said polymorphic forms, and methods for using said pharmaceutical dosage forms for the treatment of various disorders such as, CNS disorders.

The mesylate salt of the compound 7-[4-([1,1'-biphenyl]-3-ylmethyl)-1-piperazinyl]-2(3H)-benzoxazolone monomethanesulfonate (INNM bifeprunox mesylate) has the formula

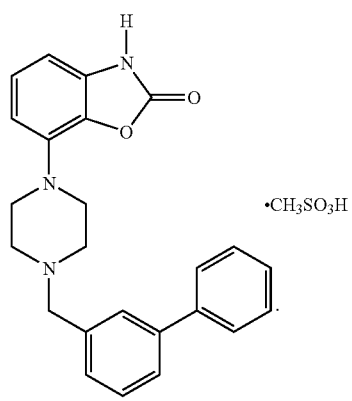

(I)

The hydrochloric acid salt of this compound (7-[4-([1,1'-biphenyl]-3-ylmethyl)-1-piperazinyl]-2(3H)-benzoxazolone (bifeprunox) is described and claimed in WO97/36893 and the monomethanesulfonate salt is described and claimed in W002/066449. In the second of these patent publications the direct formation of the monomethanesulfonate salt by the reaction between the reactive mesylate ester of N,N,N-bis(2-ethanol)-m-phenylbenzyl amine and 7-amino-2(3H)-benzoxazolone is disclosed.

It has been discovered that by the method described in W002/066449 bifeprunox mesylate is normally obtained as a crude product (melting range indicated in W002/066449 as 263-275° C.) in a polymorphic form further indicated in this application as polymorph δ (delta). Upon further purification, the product is obtained in two different crystal modifications or a mixture of these two modifications. The first of the two modifications is the already mentioned polymorph δ (delta) and has a melting point in pure form of 265° C. The second modification is further indicated as polymorph γ (gamma). When the γ polymorph is predominantly obtained, it is in almost all cases obtained in a mixture of said polymorph with polymorph δ, the mixture having a melting point of approximately 273° C.

During further investigations it appeared that polymorphs γ and δ are metastable, and therefore may have drawbacks when used in a pharmaceutical formulation. The unpredictable formation of one of the two polymorphs γ and δ or a mixture thereof is also undesirable. It would be desirable, therefore, to provide a stable crystalline form of 7-[4-([1,1'-biphenyl]-3-ylmethyl)-1-piperazinyl]-2(3H)-benzoxazolone monomethanesulfonate for pharmaceutical use which can be consistently produced.

It has surprisingly been found that 7-[4-([1,1'-biphenyl]-3-ylmethyl)-1-piperazinyl]-2(3monomethanesulfonate also has another crystalline polymorphic form (referred to below as polymorph α (alpha)) which does not have the disadvantages of the aforementioned polymorphs. This crystalline form of bifeprunox mesylate is more thermodynamically stable. Polymorphic form α does not undergo conversion, even at high atmospheric humidity or higher temperature. Furthermore this crystalline form crystallizes in the form of large crystals which can be easily filtrated and have a high purity. Therefore this polymorph α is particularly suitable for the formulation of bifeprunox mesylate in a solid form, if desired after particle size reduction.

In various embodiments, the present disclosure provides the polymorphic α form of bifeprunox mesylate at various levels of purity. In another embodiment, the present disclosure provides pharmaceutical dosage forms comprising the polymorphic a form of bifeprunox mesylate. In yet another embodiment, the present disclosure provides methods for using said dosage forms for treatment or prevention of various diseases and disorders. These embodiments, while providing some general overview of various embodiments of the present disclosure, are not intended to limit the scope of the present disclosure in any manner.

Figure 1:
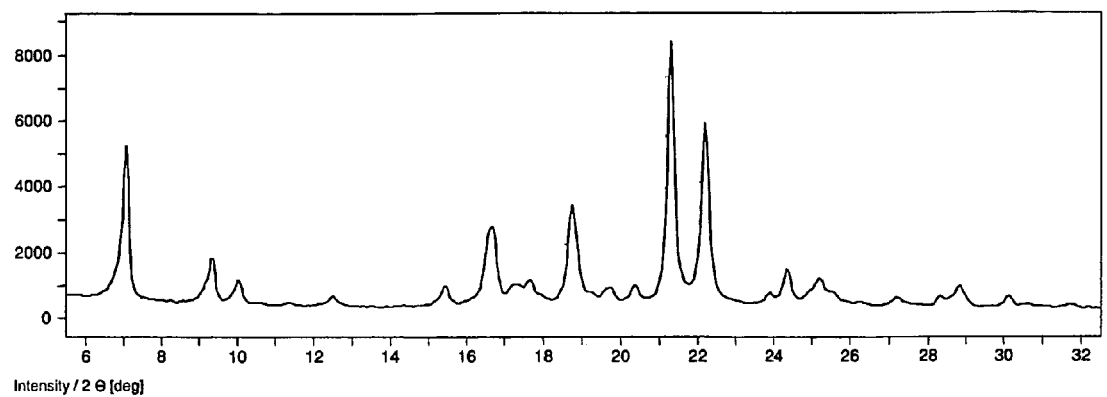
FIG. 1 shows an XRPD pattern of polymorphic form a of bifeprunox mesylate.
Figure 5:
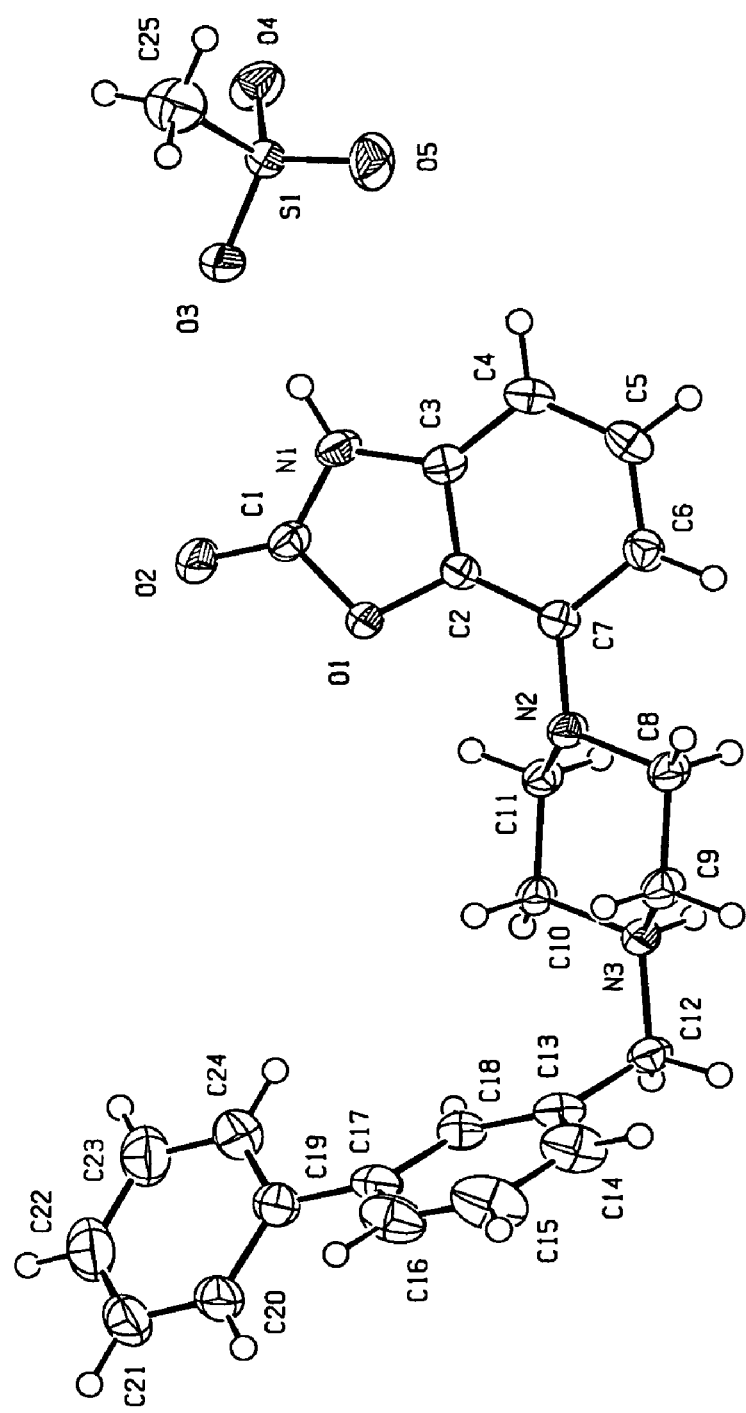
FIG. 5 shows configuration of polymorphic form a of bifeprunox mesylate derived from X-ray crystallography.
Figure 6:
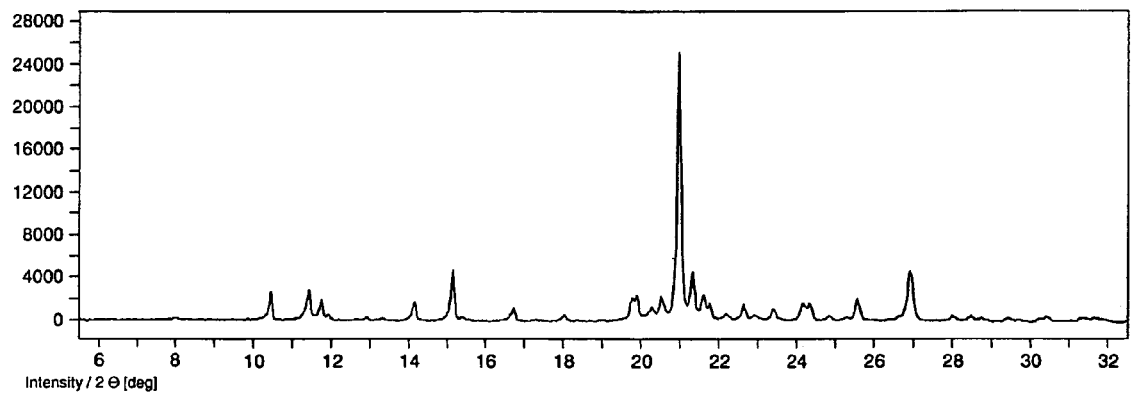
FIG. 6 shows an XRPD pattern of polymorphic form γ of bifeprunox mesylate.
Figure 7:
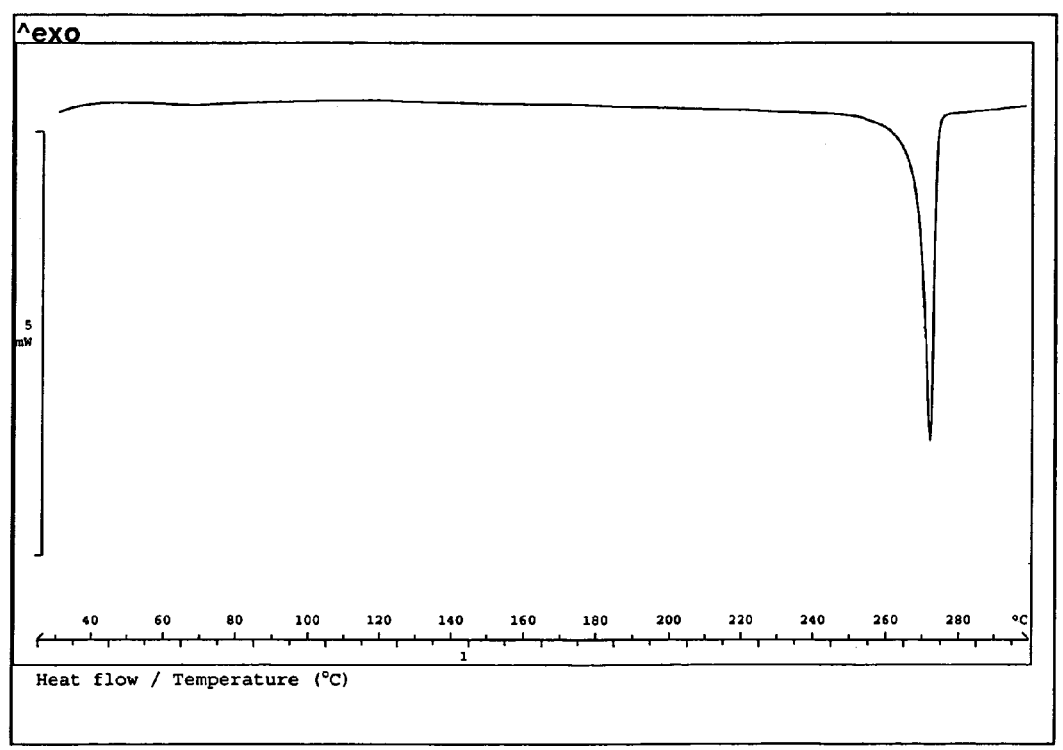
FIG. 7 shows a DSC trace of polymorphic form γ of bifeprunox mesylate.
Figure 8:
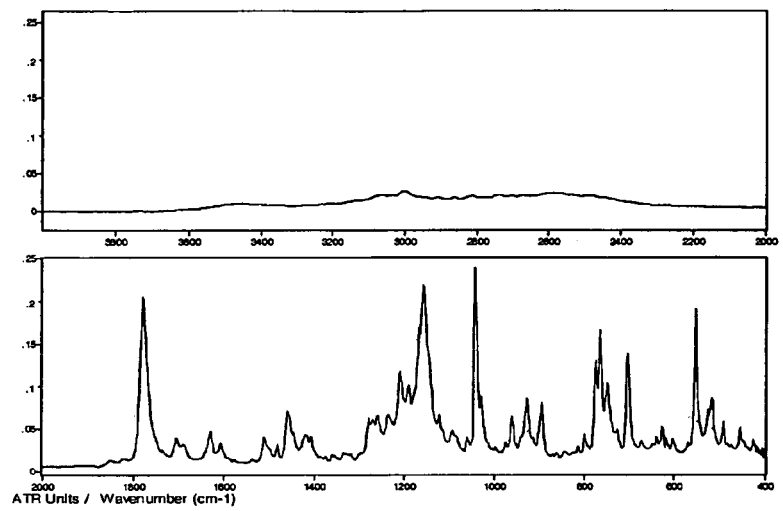
FIG. 8 shows an IR (ATR) spectrum of polymorphic form γ of bifeprunox mesylate.
Figure 9:
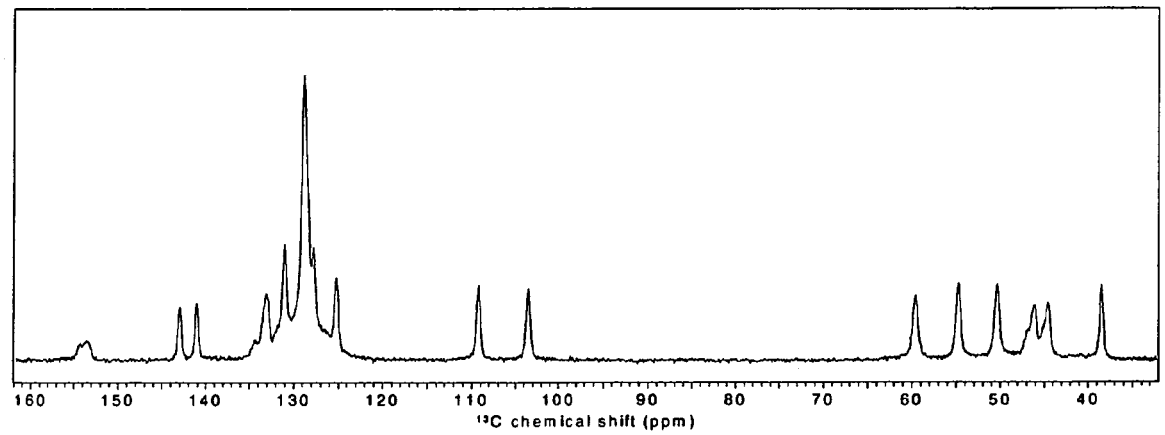
FIG. 9 shows a $^{13}C$ solid state NMR spectrum of polymorphic form γ of bifeprunox mesylate.
Figure 10:
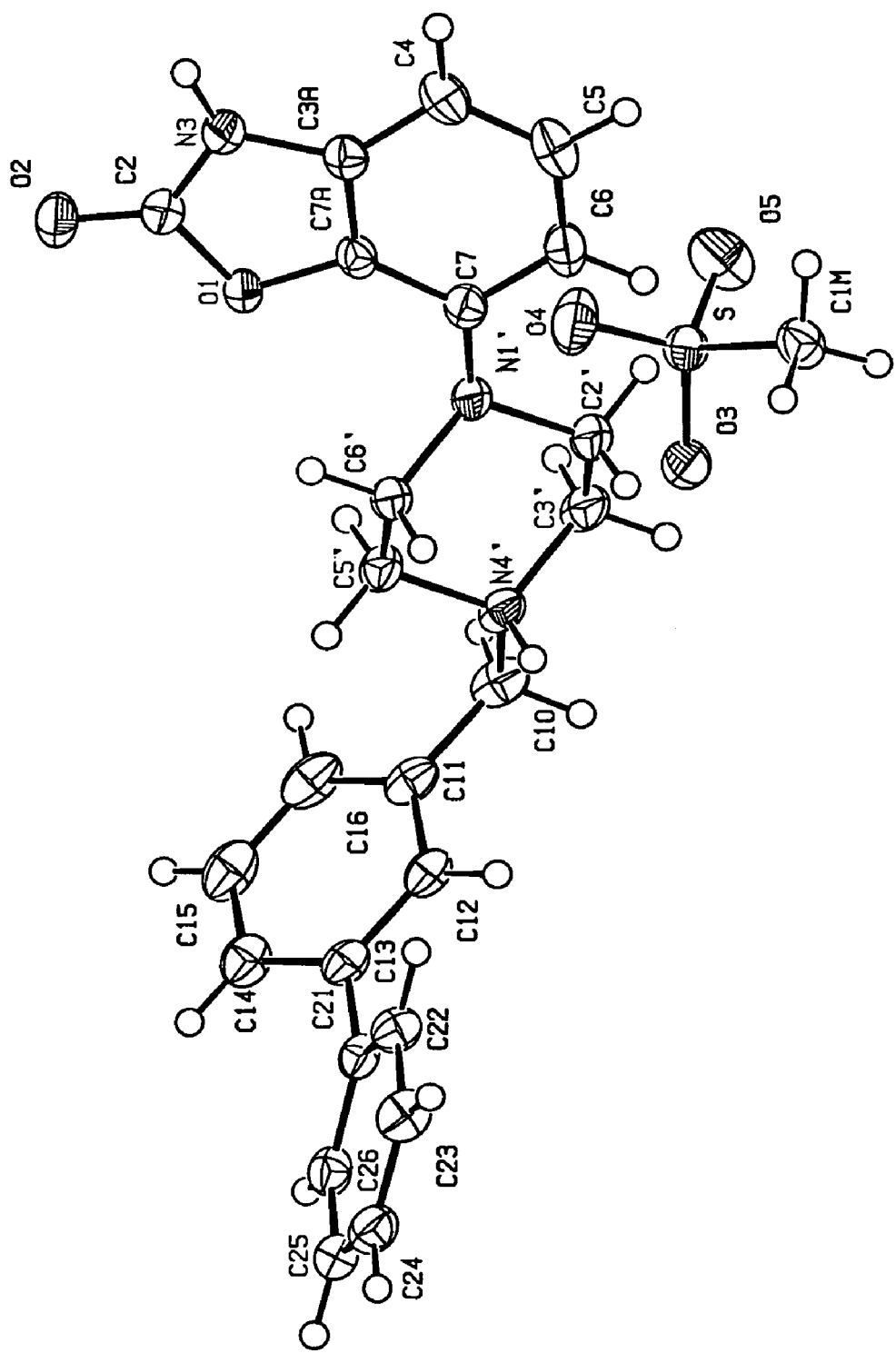
FIG. 10 shows configuration of polymorphic form γ of bifeprunox mesylate derived from X-ray crystallography.
Figure 11:
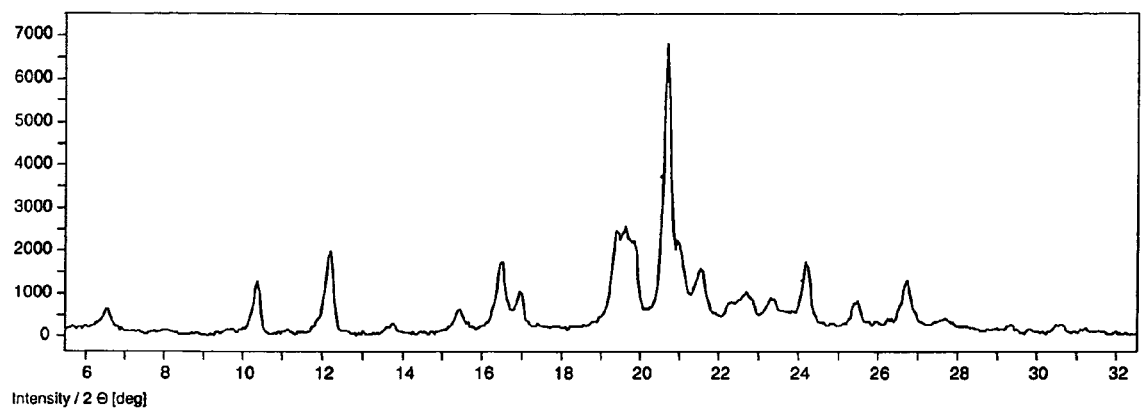
FIG. 11 shows an XRPD pattern of polymorphic form δ of bifeprunox mesylate.
Figure 12:
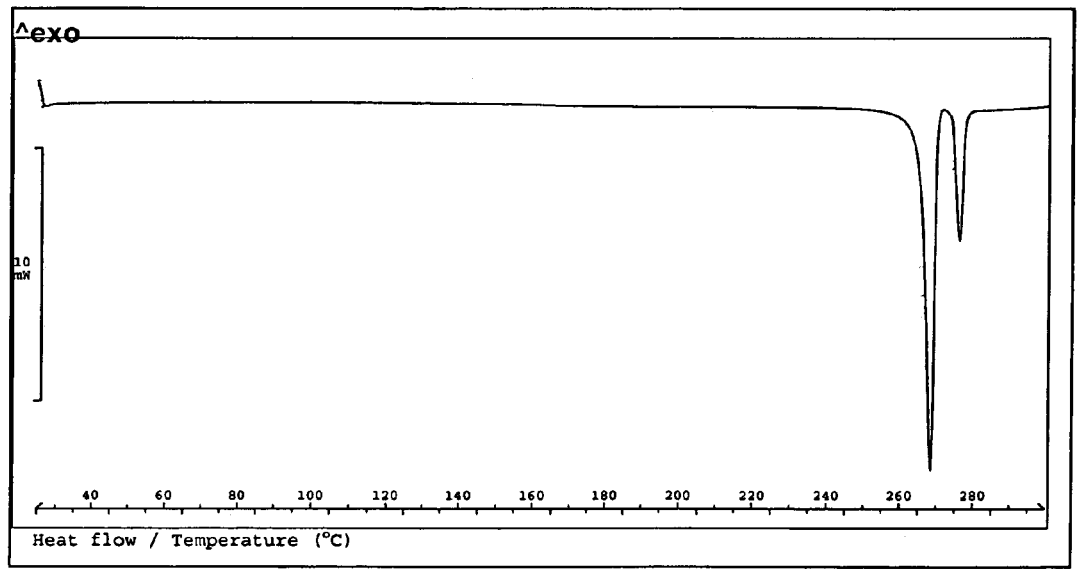
FIG. 12 shows a DSC trace of polymorphic form δ of bifeprunox mesylate.
Figure 13:
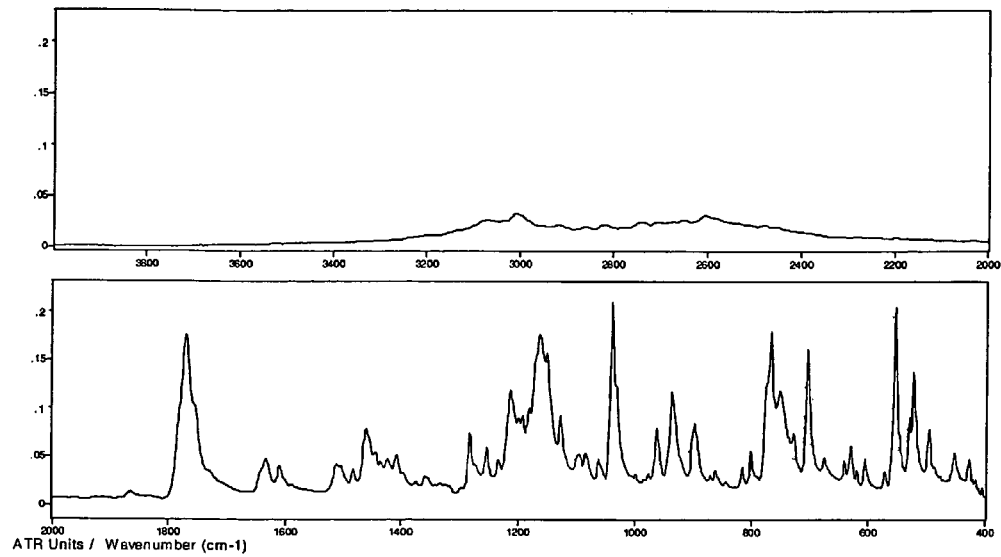
FIG. 13 shows an IR (ATR) spectrum of polymorphic form δ of bifeprunox mesylate.
Figure 14:
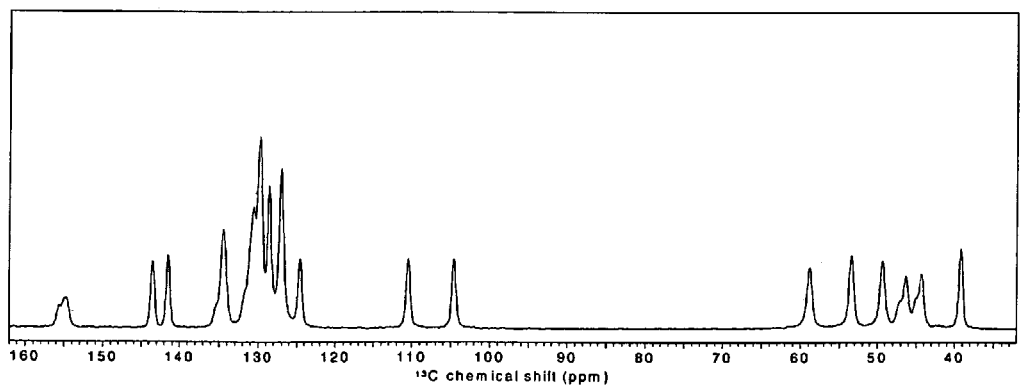
FIG. 14 shows a $^{13}C$ solid state NMR spectrum of polymorphic form δ of bifeprunox mesylate.
Figure 15:
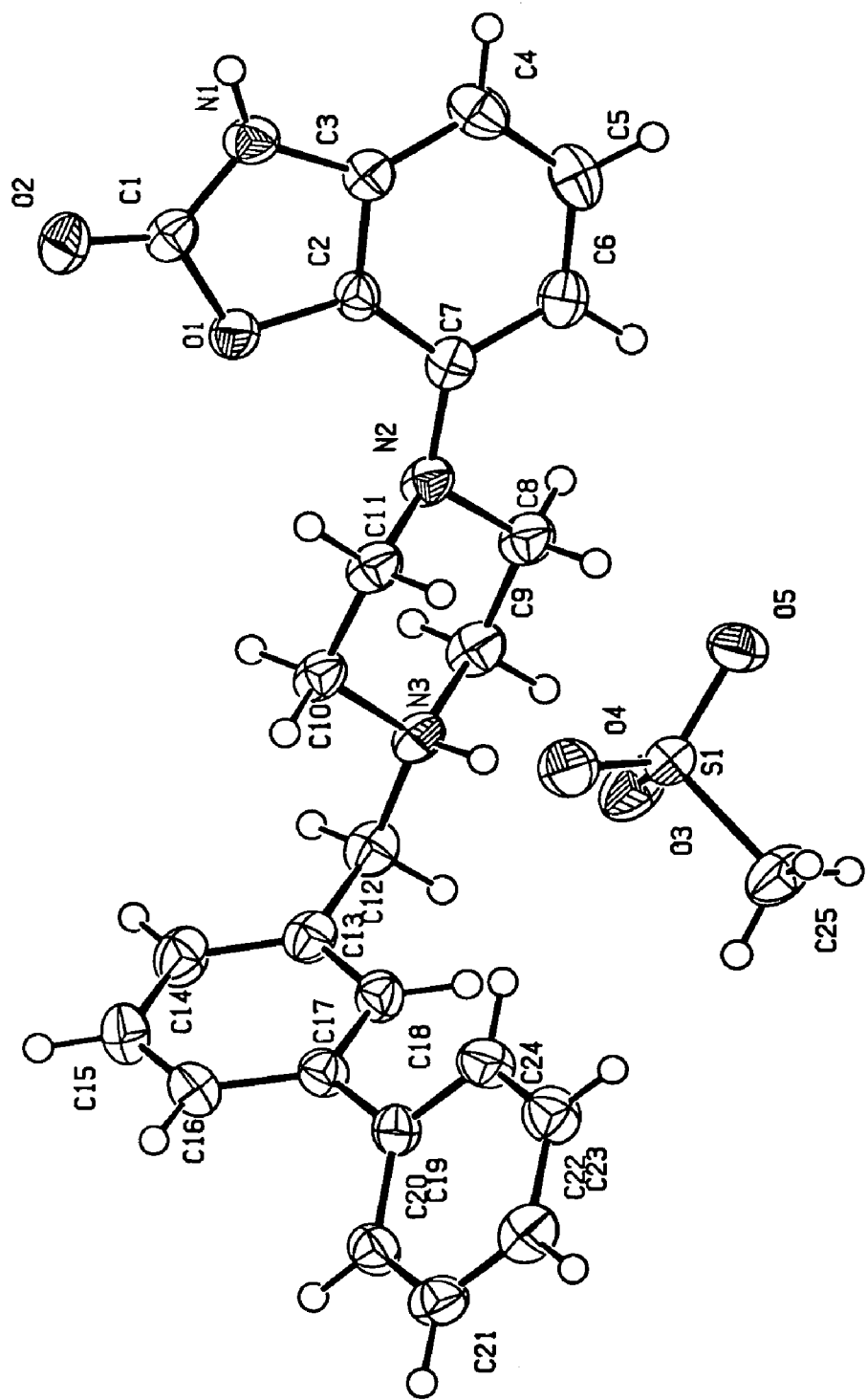
FIG. 15 shows configuration of polymorphic form δ of bifeprunox mesylate derived from X-ray crystallography.

In one embodiment, the crystalline polymorphic form of bifeprunox mesylate according to the present disclosure is defined by at least one of the following physicochemical parameters:

X-Ray diffraction patterns (Table 1 and FIG. 1);

The melting point of polymorphic form α is 277° C. (DSC heating rate 10 K/min) (see DSC thermogram, FIG. 2);

IR spectrum (Table 2 and FIG. 3), wherein the characteristic IR absorption bands of form α of bifeprunox mesylate which can be used to distinguish this form from forms γ and δ are given in Table 2a;

Solid state $^{13}$C-NMR spectrum (Table 3 and FIG. 4), wherein the characteristic $^{13}$C-NMR shifts of form α of bifeprunox mesylate which can be used to distinguish this form from forms γ and δ are given in Table 3a;

Single crystal X-ray diffraction (Tables 4 and 5 and FIG. 5).

Table 1 shows characteristic X-ray powder diffractions (XRPD) of forms α, γ and δ of bifeprunox mesylate. FIG. 1 provides a representative XRPD pattern of polymorphic form a of bifeprunox mesylate.

TABLE 1

| Form | Characteristic reflexes (expressed in degree of diffraction angle 2θ at room temperature) |
|---|---|
| α | 7.0, 9.3, 10.0, 12.5, 15.4, 16.7, 17.2, 17.4, 17.7, 18.7, 21.3, 22.2, 25.2, 27.2, 28.3, 28.8, 30.1 |
| γ | 10.4, 11.4, 11.7, 14.1, 15.1, 21.0, 26.9 |
| δ | 6.4, 10.2, 12.1, 16.4, 16.8, 19.3, 19.7, 20.6, 24.1, 26.6 |

Figure 2:
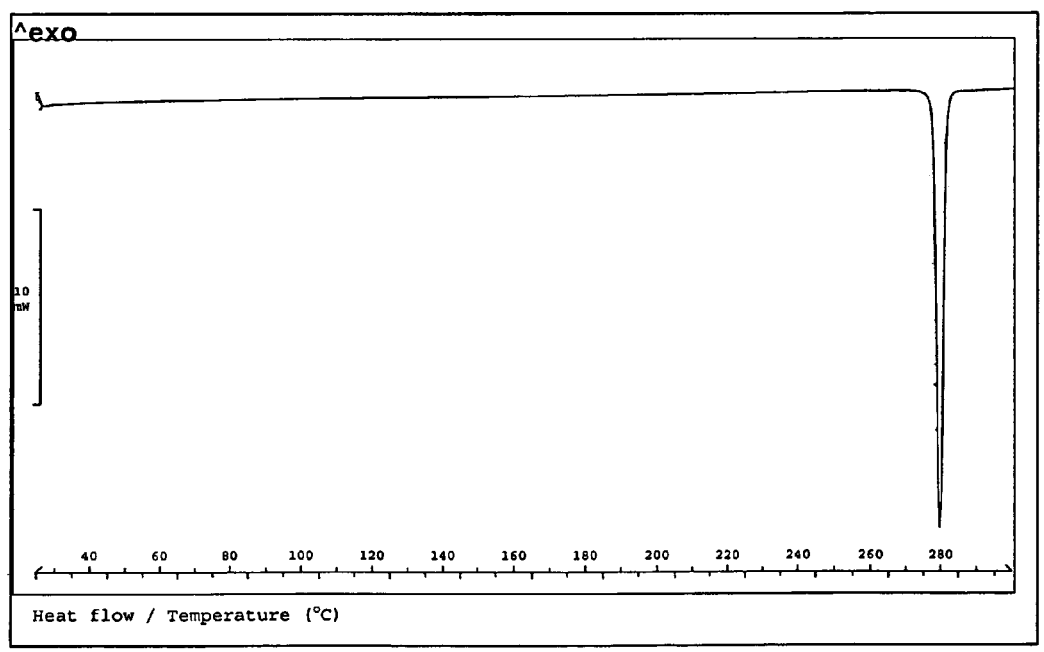
FIG. 2 shows a DSC trace of polymorphic form a of bifeprunox mesylate.

Table 2 shows characteristic IR absorption bands of forms α, γ and δ of bifeprunox mesylate. FIG. 2 provides a representative IR spectrum of polymorphic form α of bifeprunox mesylate.

TABLE 2

| Form | Characteristic IR absorption bands (expressed in cm$^{-1}$) |
|---|---|
| α | 1764, 1636, 1284, 1217, 809, 795, 746, 694, 663, 509 |
| γ | 1777, 1279, 1258, 1210, 1124, 800, 764, 749, 627, 518 |
| δ | 1865, 1769, 1434, 1282, 1253, 1212, 1126, 935, 767, 751 |

Table 2a also shows important IR absorption bands of forms α, γ and δ of bifeprunox mesylate which can be used to distinguish the three forms.

TABLE 2a

| Form | Characteristic IR absorption bands (expressed in cm$^{-1}$) |
|---|---|
| α | 1764, 1217, 795, 746, 694 |
| γ | 1777, 1210, 764, 749, 518 |
| δ | 1769, 1212, 935, 767, 751 |

Figure 3:
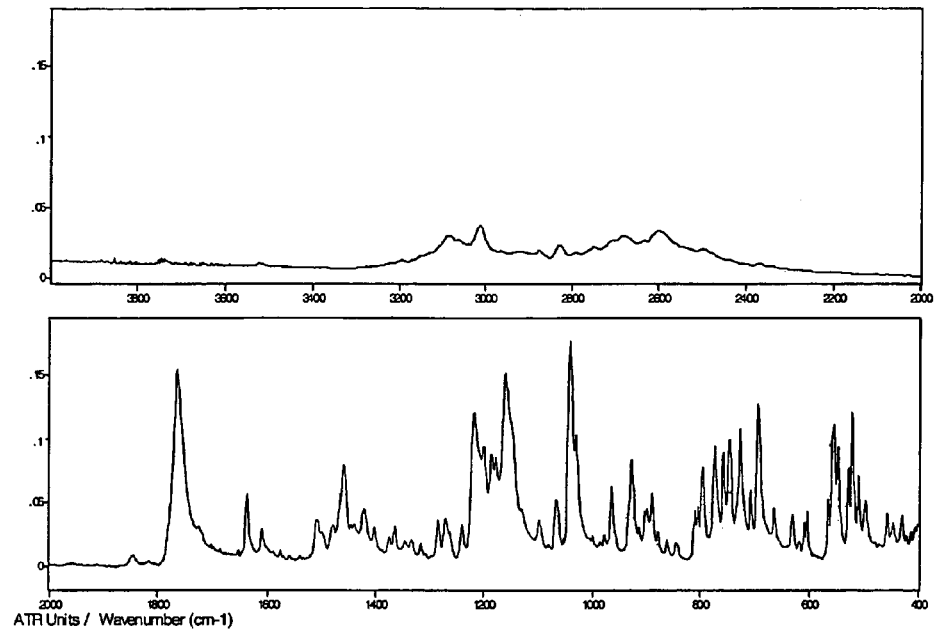
FIG. 3 shows an IR (ATR) spectrum of polymorphic form a of bifeprunox mesylate.

Table 3 shows characteristic $^{13}$C solid state NMR chemical shifts in forms α, γ and δ of bifeprunox mesylate. FIG. 3 provides a representative $^{13}$C solid state NMR spectrum of polymorphic form a of bifeprunox mesylate.

TABLE 3

| Form | Characteristic chemical shift (expressed in ppm relative to glycine ($\delta_c$ = 176.03 for the C=O resonance) |
|---|---|
| α | 40.4, 48.7, 50.3, 56.5, 106.8, 110.7, 124.9, 126.9, 127.8, 129.2, 130.8, 134.2, 137.7, 141.6, and *153.8. |
| γ | 38.2, *44.3, *45.9, 50.1, 54.5, 59.4, 103.5, 109.3, 125.3, 127.9, 128.9, 131.1, 133.2, 134.5, 141.2, 143.2 and *153.7 |
| δ | 39.1, *44.3, *46.3, 49.3, 53.4, 58.8, 104.6, 110.4, 124.6, 127.0, 128.5, 129.7, 130.5, 134.4, 141.5, 143.5, and *154.7 |

*denotes carbon resonances which show typical asymmetric residual quadrupolar splittings. Chemical shift are given for the high-field resonance maximum.

Table 3a also shows important $^{13}$C solid state NMR chemical shifts bands of forms α, γ and δ of bifeprunox mesylate which can be used to distinguish the three forms.

TABLE 3a

| Form | Characteristic chemical shift (expressed in ppm relative to glycine ($\delta_c$ = 176.03 for the C=O resonance) |
|---|---|
| α | 40.4, 48.7, 56.5, 106.8 and 137.7 |
| γ | 38.2, 54.5, 103.5, 109.3 and 133.2 |
| δ | 39.1, 49.3, 53.4, 58.8 and 104.6 |

Table 4 shows relevant Single Crystal X-ray Diffraction data collection parameters for the crystal structure determination of forms α, γ and δ of bifeprunox mesylate.

TABLE 4

| | Alpha (α) | Gamma (γ) | Delta (δ) |
|---|---|---|---|
| Temperature (K) | 150 | 133 | 150 |
| Wavelength (Å) | 0.71073[1] | 0.71073 | 0.71073 |
| Crystal size (mm × mm × mm) | 0.10 × 0.15 × 0.27 | 0.24 × .13 × 0.07 | 0.10 × 0.15 × 0.35 |
| Crystal system | triclinic | monoclinic | triclinic |
| Space group | P-1 | P2$_1$/c | P-1 |
| Z | 2 | 4 | 2 |
| Unit cell dimensions; A (Å) | 9.823 | 9.0975 | 9.1832 |
| B (Å) | 10.737 | 15.269 | 9.3963 |
| C (Å) | 12.690 | 17.128 | 14.106 |
| α (°) | 98.553 | 90 | 76.968 |
| β (°) | 93.749 | 100.694 | 83.809 |
| Γ (°) | 116.097 | 90 | 89.157 |
| Calculated density (g cm$^{-3}$) | 1.481 | 1.368 | 1.3556 |
| Completeness of data (%) | 100.0 | 100.0 | 99.8 |
| Total number of reflections | 27105 | 23759 | 27207 |
| Number of unique reflections | 5355 | 5809 | 4149 |
| Nr. Of refined parameters | 314 | 316 | 314 |

[1] (Mo Kα radiation)

Table 5 shows atomic coordinates (×10$^4$) and equivalent isotropic displacement parameters (Å$^2$×10$^3$) of crystal structure of form a of bifeprunox mesylate. U(eq) is defined as one third of the trace of the orthogonalized U$_{ij}$ tensor.

TABLE 5

|  | x | y | z | U(eq) |
|---|---|---|---|---|
| O1 | 3471.7(11) | 3848.0(10) | 2910.8(8) | 26.4(3) |
| O2 | 2785.8(13) | 1499.8(11) | 2541.1(10) | 38.1(4) |
| N1 | 5215.5(15) | 3175.4(14) | 3398.0(11) | 29.3(4) |
| N2 | 3880.6(13) | 6773.4(13) | 3211.0(10) | 24.6(4) |
| N3 | 1702.0(14) | 7879.1(13) | 3177.7(11) | 24.9(4) |
| C1 | 3755.9(18) | 2687.4(17) | 2914.9(13) | 28.6(5) |
| C2 | 4801.7(16) | 5042.8(16) | 3421.0(12) | 23.7(4) |
| C3 | 5896.6(17) | 4637.6(16) | 3727.8(12) | 25.8(5) |
| C4 | 7334.0(17) | 5622.3(17) | 4265.8(12) | 28.3(5) |
| C5 | 7587.8(18) | 7016.7(18) | 4470.3(12) | 30.7(5) |
| C6 | 6489.3(17) | 7425.7(17) | 4145.1(12) | 28.2(5) |
| C7 | 5035.3(17) | 6432.4(16) | 3594.8(12) | 24.3(4) |
| C8 | 4371.2(18) | 8285.6(16) | 3280.4(14) | 29.8(5) |
| C9 | 3141.4(17) | 8515.3(17) | 2694.6(13) | 29.2(5) |
| C10 | 1196.3(17) | 6328.4(15) | 3094.7(13) | 25.8(5) |
| C11 | 2450.2(16) | 6106.0(13) | 3661.4(12) | 25.9(5) |
| C12 | 465.7(18) | 8238.1(17) | 2763.9(13) | 29.1(5) |
| C13 | −273.5(18) | 7526.6(18) | 1622.4(13) | 30.9(5) |
| C14 | 166(2) | 8245(2) | 780.4(15) | 46.7(7) |
| C15 | −586(2) | 7574(3) | −256.4(16) | 57.6(8) |
| C16 | −1734(2) | 6194(2) | −466.0(15) | 49.2(7) |
| C17 | −2206.8(19) | 5456.1(19) | 362.2(13) | 34.9(6) |
| C18 | −1474.4(18) | 6157.3(18) | 1409.5(13) | 30.8(5) |
| C19 | −3495(2) | 4003.7(19) | 170.3(13) | 37.1(6) |
| C20 | −4751(2) | 3585(2) | −623.3(14) | 43.7(6) |
| C21 | −5976(2) | 2260(2) | −766.8(17) | 54.6(7) |
| C22 | −5989(2) | 1318(2) | −129.3(18) | 58.2(8) |
| C23 | −4750(3) | 1709(2) | 655.0(17) | 54.6(7) |
| C24 | −3520(2) | 3039(2) | 804.2(15) | 45.3(6) |
| S1 | 8220.4(4) | 1865.1(4) | 3801.4(3) | 26.8(1) |
| O3 | 6650.8(13) | 1454.8(12) | 3355.9(10) | 40.2(4) |
| O4 | 8282.1(15) | 1197.6(13) | 4711.2(9) | 42.6(4) |
| O5 | 9171.5(14) | 3369.6(12) | 4040.9(11) | 48.7(4) |
| C25 | 8951(2) | 1114(2) | 2801.2(15) | 51.0(7) |

Table 6 shows atomic coordinates (×10$^4$) and equivalent isotropic displacement parameters (Å$^2$×10$^3$) of crystal structure of form γ of bifeprunox mesylate. U(eq) is defined as one third of the trace of the orthogonalized U$_{ij}$ tensor.

TABLE 6

|  | x | y | z | U(eq) |
|---|---|---|---|---|
| O(1) | 6610.7(11) | 756.7(7) | 6306.4(6) | 26.6(2) |
| O(2) | 9117.5(12) | 552.8(8) | 6513.4(8) | 40.3(3) |
| C(2) | 7882.4(17) | 240.9(11) | 6352.9(10) | 29.1(4) |
| N(3) | 7439.1(14) | −598.9(9) | 6206.3(9) | 27.4(3) |
| C(3A) | 5878.6(17) | −646.4(10) | 6063.5(9) | 24.5(3) |
| C(4) | 4896.5(18) | −1346.6(11) | 5948.7(9) | 31.7(4) |
| C(5) | 3392.7(19) | −1133.4(11) | 5866.9(10) | 35.5(4) |
| C(6) | 2894.2(18) | −281.1(11) | 5915.0(9) | 32.3(4) |
| C(7) | 3884.2(17) | 428.8(10) | 6069.0(9) | 26.2(3) |
| C(7A) | 5382.3(16) | 199.5(10) | 6119.9(8) | 23.7(3) |
| N(1') | 3465.6(14) | 1286.2(8) | 6230.9(8) | 28.4(3) |
| C(2') | 1876.4(18) | 1434.5(11) | 6215.9(11) | 35.7(4) |
| C(3') | 1661.2(18) | 2283.3(11) | 6630.8(12) | 36.5(4) |
| N(4') | 2322.4(14) | 3039.8(9) | 6262.9(8) | 28.0(3) |
| C(5') | 3942.4(17) | 2861.2(11) | 6265.4(10) | 30.0(4) |
| C(6') | 4103.6(17) | 2010.2(10) | 5840.3(9) | 27.2(3) |
| C(10) | 2051(2) | 3884.9(11) | 6667.0(10) | 35.6(4) |
| C(11) | 2788.0(18) | 4658.9(11) | 6354.9(9) | 30.7(4) |
| C(12) | 2314.0(17) | 4949.2(10) | 5577.8(9) | 27.8(4) |
| C(13) | 3015.0(17) | 5646.9(10) | 5277.0(9) | 26.8(3) |
| C(14) | 4183.8(18) | 6072.6(11) | 5781.3(10) | 33.7(4) |
| C(15) | 4644(2) | 5795.6(12) | 6554.8(11) | 40.5(4) |
| C(16) | 3964.4(19) | 5086.4(12) | 6836.9(10) | 38.5(4) |
| C(21) | 2576.4(16) | 5917.7(10) | 4432.7(9) | 25.3(3) |
| C(22) | 2266.8(17) | 5286.3(11) | 3836.1(9) | 29.8(4) |

TABLE 6-continued

|  | x | y | z | U(eq) |
|---|---|---|---|---|
| C(23) | 1921.6(19) | 5532.9(11) | 3043.3(10) | 35.0(4) |
| C(24) | 1900.5(18) | 6409.3(11) | 2833.0(10) | 33.3(4) |
| C(25) | 2200.7(17) | 7041.3(11) | 3419.1(10) | 31.8(4) |
| C(26) | 2519.2(17) | 6797.7(10) | 4209.4(10) | 29.3(4) |
| S | 9163.9(4) | −2786.7(3) | 5975.1(2) | 28.4(1) |
| O(3) | 9584.0(13) | −1870.9(7) | 6067.6(8) | 39.5(3) |
| O(4) | 7714.0(13) | −2961.4(8) | 6156.0(8) | 48.0(4) |
| O(5) | 9327.4(15) | −3123.8(9) | 5197.7(7) | 50.7(4) |
| C(1M) | 10484.0(18) | −3388.0(11) | 6647.3(9) | 33.1(4) |

Table 7 shows atomic coordinates (×10$^4$) and equivalent isotropic displacement parameters (Å$^2$×10$^3$) of crystal structure of form δ of bifeprunox mesylate. U(eq) is defined as one third of the trace of the orthogonalized U$_{ij}$ tensor.

TABLE 7

|  | x | y | z | U(eq) |
|---|---|---|---|---|
| O1 | 4353.9(14) | 2151.8(14) | 9.8(9) | 31.7(5) |
| O2 | 2013.8(15) | 1799.9(16) | −260.0(11) | 41.7(6) |
| N1 | 3473.0(19) | 3697(2) | −1220.7(13) | 33.0(6) |
| N2 | 7357.2(17) | 2103.5(19) | 550.2(12) | 32.1(6) |
| N3 | 8449.3(17) | 325.4(19) | 2265.2(12) | 30.5(6) |
| C1 | 3130(2) | 2515(2) | −491.7(15) | 31.6(8) |
| C2 | 5441(2) | 3184(2) | −431.7(14) | 27.6(7) |
| C3 | 4912(2) | 4146(2) | −1202.7(15) | 29.5(7) |
| C4 | 5792(2) | 5233(2) | −1804.5(16) | 38.0(8) |
| C5 | 7222(2) | 5295(2) | −1576.5(17) | 40.4(8) |
| C6 | 7745(2) | 4328(2) | −796.9(16) | 35.7(8) |
| C7 | 6862(2) | 3203(2) | −190.9(15) | 29.9(7) |
| C8 | 8926(2) | 2107(2) | 662.0(15) | 36.3(8) |
| C9 | 9346(2) | 659(2) | 1284.5(15) | 36.0(7) |
| C10 | 6854(2) | 364(2) | 2127.3(15) | 33.3(7) |
| C11 | 6484(2) | 1826(2) | 1508.8(14) | 34.0(7) |
| C12 | 8900(2) | −1091(2) | 2896.8(15) | 35.7(8) |
| C13 | 7978(2) | −1468(2) | 3868.2(15) | 32.6(7) |
| C14 | 6997(2) | −2644(2) | 4086.9(17) | 40.5(8) |
| C15 | 6109(2) | −2941(2) | 4966.4(17) | 42.7(8) |
| C16 | 6171(2) | −2068(2) | 5624.7(16) | 39.1(8) |
| C17 | 7146(2) | −888(2) | 5437.5(15) | 32.1(7) |
| C18 | 8054(2) | −613(2) | 4552.0(15) | 32.2(7) |
| C19 | 7171(2) | 74(2) | 6137.9(15) | 31.4(7) |
| C20 | 7068(2) | −494(2) | 7144.3(15) | 34.8(7) |
| C21 | 7028(2) | 422(3) | 7794.2(16) | 38.2(8) |
| C22 | 7099(2) | 1919(3) | 7448.1(16) | 39.7(8) |
| C23 | 7201(2) | 2497(2) | 6453.5(16) | 41.0(8) |
| C24 | 7234(2) | 1589(2) | 5798.4(16) | 37.9(8) |
| S1 | 8731.8(6) | 3909.1(6) | 3076.9(4) | 33.3(2) |
| O3 | 9471.7(16) | 2602.8(16) | 2887.4(12) | 50.3(6) |
| O4 | 7233.7(16) | 3640.6(18) | 3484.5(11) | 50.4(6) |
| O5 | 8877.7(16) | 5117.0(17) | 2228.8(11) | 47.6(5) |
| C25 | 9712(3) | 4404(3) | 3958.1(17) | 48.8(9) |

The polymorphic form a differs substantially from the forms γ and δ in its physicochemical parameters: DSC melting behavior, X-ray diffraction pattern, IR spectrum and solid state $^{13}$C-NMR spectrum. The physicochemical parameters of the forms γ and δ are given in Tables 1-4, 6 and 7 and FIGS. 6-15.

In another embodiment, the present disclosure provides bifeprunox mesylate in which at least about 50 percent by weight (wt. %), at least about 60 wt. %, at least about 70 wt. %, at least about 80 wt. %, at least about 90 wt. %, or at least about 95 wt. % of the bifeprunox mesylate is in the polymorphic α form. In other embodiment, such embodiments are substantially devoid of any γ or δ polymorphic forms of bifeprunox mesylate. In another embodiment, the bifeprunox mesylate provided by the present disclosure comprises less than 10 wt. %, less than 5 wt. %, or less than 2.5 wt. % of the γ or δ polymorphic forms of bifeprunox mesylate. In another embodiment, at least about 99 wt. % of bifeprunox mesylate is in the polymorphic a form.

In one embodiment, the preparation of the polymorphic form α is carried out by recrystallization from an organic solvent or a mixture of an organic solvent with water, preferably a mixture of a ($C_1$-$C_6$) alcohol and water or a mixture of acetonitrile and water. In another embodiment, the solvent is a mixture is 2-propanol and water or a mixture of acetonitrile and water. In another embodiment, the solvent is a mixture of acetonitrile and water. The polymorphic form γ can be prepared by making the free base of bifeprunox directly followed by the addition of methane sulphonic acid and crystallization from methylethylketone.

The polymorphic form α and γ according to the present disclosure can be formulated into dosage forms in which the crystalline active substance is present in the solid form by methods known in the art. Examples of said dosage forms are (optionally coated) tablets, capsules, granular aerosols, suppositories and suspensions. Such dosage forms can be prepared by mixing the polymorphic form α or γ of the active substance with inert pharmaceutically acceptable excipients and carriers.

In one embodiment, one to a small plurality (e.g. 1 to about 4) of dosage units of a composition of the present disclosure comprise about 0.05 to about 40 mg, about 0.75 to about 35 mg, about 0.1 to about 30 mg or about 0.125 to about 20 mg of bifeprunox mesylate (in α, δ, and/or γ form) per dosage unit. Illustratively, such a dosage unit can comprise 0.125 mg, 1 mg, 5 mg, 10 mg, or 20 mg of bifeprunox mesylate.

Compositions of the present disclosure can comprise one or more pharmaceutical excipients. Non-limiting examples of suitable excipients include suspending agents (for example, gums, xanthans, cellulosics and sugars), humectants (for example, sorbitol), solubilizers (for example, ethanol, water, PEG and propylene glycol), surfactants (for example, sodium lauryl sulfate, Spans, Tweens, and cetyl pyridine), preservatives, antioxidants (for example, parabens, and vitamins E and C), anti-caking agents, coating agents, chelating agents (for example, EDTA), stabilizers, antimicrobial agents, anti-fungal or antibacterial agents (for example, parabens, chlorobutanol, phenol, sorbic acid), isotonic agents (for example, sugar, sodium chloride), thickening agents (for example, methyl cellulose), flavoring agents (for example, chocolate, thalmantine, aspartame, root beer or watermelon or other flavorings stable at pH 7 to 9), anti-foaming agents (e.g., simethicone, Mylicon®), disintegrants, flow aids, lubricants, adjuvants, colorants, diluents, moistening agents, preservatives, carriers, binders (for example, hydroxypropylmethylcellulose, polyvinyl pyrilodone, other cellulosic materials and starch), diluents (for example, lactose and other sugars, starch, dicalcium phosphate and cellulosic materials), disintegrating agents (for example, starch polymers and cellulosic materials), glidants and water insoluble or water soluble lubricants or lubricating agents.

One illustrative dosage form comprises, apart from the milled and sieved active substance (bifeprunox as described herein), lactose monohydrate, microcrystalline cellulose, sodium starch glycolate (for example, type A), sodium stearyl fumarate and optionally colloidal anhydrous silica. In one embodiment, lactose is present in an amount of about 20% to about 90% by weight, about 70% to about 90% by weight, or about 75% to about 85% by weight, based on the total weight of the tablet core. Microcrystalline cellulose is present in an amount of about 5% to about 90% by weight, about 10% to about 15% by weight, or about 11% to about 12% by weight, based on the total weight of the tablet core. Sodium starch glycolate (e.g. type A) is present in an amount of about 0.1% to about 2.5% by weight, about 0.3% to about 0.7% by weight, or about 0.5% by weight, based on the total weight of the tablet core. Sodium stearyl fumarate is present in an amount of about 0.1% to about 1.5% by weight, about 0.6% to about 1.3% by weight, or about 1.0% by weight, based on the total weight of the tablet core. Colloidal anhydrous silica is optionally added to the formulation in order to improve the flow properties of the powder. If desired, colloidal anhydrous silica is typically present in an amount of about 0.05% to about 0.5% by weight or about 0.4% by weight, based on the total weight of the tablet core. The amount of optional coating is about 2.0% to about 5.0% by weight, about 3.0% to about 4.0% by weight, or about 3.5% by weight, based on the total weight of the tablet core.

In another embodiment, the present disclosure relates to a method of producing the formulation described above, wherein the active substance having the polymorphic form α or γ according to the present disclosure is milled and subsequently using a suitable mixer (e.g. an orbital screw mixer (Nauta mixer) or a combination of a diffusion mixer (bin blender) with a rotating impeller mill (quadro co-mill)) with lactose monohydrate, microcrystalline cellulose, sodium starch glycolate type A, sodium stearyl fumarate and optionally with colloidal anhydrous silica. The mixture is then pressed into tablets of the desired active ingredient strength. During tabletting any suitable pressure can be used, for example about 200 MPa to about 400 MPa, about 250 MPa to about 350 MPa, or about 300 MPa. The dosage form is optionally coated with a color and taste coating by spraying of a coating suspension onto the tablet core using any suitable coating equipment (e.g. a perforated pan coater or a fluidized bed coater).

Pharmaceutical compositions comprising the polymorphic form a and/or γ according to the present disclosure can be administered to a subject, for example a human subject, in need thereof. Such compositions are useful for, inter alia, the treatment of humans suffering from psychotic disorders (e.g. schizophrenia) or Parkinson's disease.

In one embodiment of the present disclosure, upon oral administration of a composition of the present disclosure to a human subject (or a plurality thereof), for example a fasted adult human subject, the subject exhibits a plasma $T_{max}$ (or a mean plasma $T_{max}$ if administered to a plurality of human subjects) of bifeprunox within about 3 hours, within about 2.8 hours, within about 2.7 hours, within about 2.6 hours, within about 2.5 hours, within about 2.4 hours, within about 2.3 hours, within about 2.2 hours, within about 2.1 hours or within about 2 hours. The term "$T_{max}$" refers to the time at which the maximum plasma concentration of bifeprunox is attained following administration of bifeprunox mesylate to the subject.

In another embodiment of the present disclosure, upon oral administration of a composition of the present disclosure to a human subject (or a plurality thereof), for example a fasted adult human subject, the subject exhibits a plasma $C_{max}$ (or a mean $C_{max}$ if administered to a plurality of human subjects) of bifeprunox of at least about 0.1 ng/ml, at least about 0.12 ng/ml, at least about 0.13 ng/ml, at least about 0.14 ng/ml, at least about 0.15 ng/ml, at least about 0.16 ng/ml, at least about 0.17 ng/ml, at least about 0.18 ng/ml, at least about 0.19 ng/ml, at least about 0.2 ng/ml, at least about 0.21 ng/ml, at least about 0.22 ng/ml, at least about 0.23 ng/ml, at least about 0.24 ng/ml, at least about 0.25 ng/ml, at least about 0.26 ng/ml, at least about 0.27 ng/ml, or at least about 0.28 ng/ml. The term "$C_{max}$" refers to the maximum plasma concentration of bifeprunox.

In another embodiment of the present disclosure, upon oral administration of a composition of the present disclosure to a human subject (or a plurality thereof), for example a fasted adult human subject, the subject exhibits a plasma $AUC_{0-24}$ (or a mean plasma $AUC_{0-24}$ if administered to a plurality of human subjects) of bifeprunox of at least about 0.9 hr·ng/ml, 1.0 hr·ng/ml, 1.1 hr·ng/ml, 1.2 hr·ng/ml, 1.3 hr·ng/ml, or 1.4 hr·ng/ml. The term "$AUC_{0-24}$" refers to the area under the plasma concentration versus time curve for the twenty-four hour period after administration.

In still another embodiment, upon oral administration of a composition of the present disclosure to a human subject (or a plurality thereof), for example a fasted adult human subject, the subject exhibits at least one of:

A. A plasma $T_{max}$ (or a mean $T_{max}$ if administered to a plurality of human subjects) of bifeprunox within about 3 hours, within about 2.8 hours, within about 2.7 hours, within about 2.6 hours, within about 2.5 hours, within about 2.4 hours, within about 2.3 hours, within about 2.2 hours, within about 2.1 hours or within about 2 hours;

B. A plasma $C_{max}$ (or a mean $C_{max}$ if administered to a plurality of human subjects) of bifeprunox of at least about 0.1 ng/ml, at least about 0.12 ng/ml, at least about 0.13 ng/ml, at least about 0.14 ng/ml, at least about 0.15 ng/ml, at least about 0.16 ng/ml, at least about 0.17 ng/ml, at least about 0.18 ng/ml, at least about 0.19 ng/ml, at least about 0.2 ng/ml, at least about 0.21 ng/ml, at least about 0.22 ng/ml, at least about 0.23 ng/ml, at least about 0.24 ng/ml, at least about 0.25 ng/ml, at least about 0.26 ng/ml, at least about 0.27 ng/ml, or at least about 0.28 ng/ml; or C. A plasma $AUC_{0-24}$ (or a mean $AUC_{0-24}$ if administered to a plurality of human subjects) of bifeprunox of at least about 0.9 hr·ng/ml, 1.0 hr·ng/ml, 1.1 hr·ng/ml, 1.2 hr·ng/ml, 1.3 hr·ng/ml, or 1.4 hr·ng/ml.

U.S. patent application Ser. Nos. 10/920,361 and 10/920,386 are hereby incorporated herein by reference in their entireties. All data herein are understood to be approximate and subject to normal measurement error depending, for example, on the apparatus used and other parameters influencing peak positions and peak intensities. Unless specifically defined otherwise or unless the context demands otherwise, the word "about" as used herein generally means ±5% of the recited value.

EXAMPLES

The following examples are only intended to further illustrate the present disclosure, in more detail, and therefore these examples are not deemed to restrict the scope of the present disclosure in any way.

Example 1

Preparation of Bifeprunox Mesylate

Example 1a

Preparation of
N-(5-chloro-2-hydroxyphenyl)acetamide 143.6 g (1 mole) of 2-amino-4-chlorphenol was suspended in 550 ml of methyl t-butyl ether under mild nitrogen purge. The mixture was heated to reflux until the material was dissolved. After 40 minutes, 112.3 g of acetic anhydride was added. After the addition the mixture was cooled to 20-25° C. in one hour. After stirring for an additional hour the mixture was cooled to 0-5° C. under stirring and kept on this temperature for an additional hour. The product was filtered off, washed with 200 ml of methyl t-butyl ether twice and dried at 50° C. and 100 mbar under a gentle nitrogen stream till dry. Yield about 92%.

Example 1b

Preparation of
N-(5-chloro-2-hydroxy-3-nitrophenyl)acetamide 224.5 g of sulphuric acid (50% w/w) was dissolved in 300 ml of water and cooled to 25° C. while stirring under a mild nitrogen purge. 185.1 g (1 mole) of N-(5-chloro-2-hydroxyphenyl)acetamide prepared according to Example 1a was added to the diluted sulphuric acid and mixed intensively. 4 ml of nitric acid 65% w/w was added to the foam formed on top of the reaction mixture at low stirring speed. The stirring speed was increased and 75 ml of nitric acid 65% w/w was added in 45 minutes, while maintaining the temperature between 23 and 26° C. The mixture was stirred vigorously for an additional 1 hour at 23-26° C. Then the mixture was cooled to 0-5° C. and vigorously stirred at this temperature for 1 hour. The solid was filtered off quickly, washed three times with 300 ml of cold water, sucked for at least 30 minutes and dried at 50° C. and 100 mbar under a gentle nitrogen stream till dry.

The crude product was suspended in 2000 ml 96% ethanol, heated till reflux and refluxed under stirring for about 15 minutes until a clear solution was obtained. The solution was cooled to 25-30° C. in about 1 hour, while stirring slowly, further cooled to 0-5° C. and stirred at this temperature for an additional hour. The solid was filtered off, washed twice with 250 ml of cold 96% ethanol, and dried at 50° C. and 100 mbar under a gentle nitrogen stream till dry. Yield about 78%.

Example 1c

Preparation of 6-amino-4-chloro-2-nitrophenol 230.6 g (1 mole) of N-(5-chloro-2-hydroxy-3-nitrophenyl)acetamide prepared according to Example 1b was suspended in a mixture of 950 ml of water and 100 ml of 2-propanol under a mild nitrogen purge. 345 ml of 36% w/w hydrochloric acid was added followed by 25 ml of water. The mixture was heated to reflux in about 30° C., while vigorously stirring and refluxed for 2 hours. The mixture was cooled to 0-5° C. in about one hour and stirred for an additional hour at 0-5° C. The solid was filtered off, washed twice with 250 ml of water, and dried at 50° C. and 100 mbar under a gentle nitrogen stream till dry. Yield about 91%.

Example 1d

Preparation of
5-chloro-7-nitro-2(3H)-benzoxazolone 188.6 g (1 mole) of 6-amino-4-chloro-2-nitrophenol prepared according to Example 1c was suspended in 1000 ml of ethyl acetate under mild nitrogen purge and the optional present water was removed by azeotropic distillation of 250 ml of the solvent. The mixture was cooled to 20-25° C. and 224 g of carbonyldiimidazole was added as a slurry in 650 ml of ethyl acetate. An additional 100 ml of ethyl acetate was added and the mixture was vigorously stirred during two hours, without the application of cooling. 1000 ml of water was added and the mixture was stirred for 15 minutes. 1450-1500 ml of ethyl acetate was distilled off at about 200 mBar and about 50° C. The mixture was cooled to 0-5° C., 225 ml of 36% HCl was added and the mixture was cooled again to 0-5° C. and stirred at this temperature for 15 minutes. The solid was filtered off, washed with 400 ml of 1N HCl, washed twice with 500 ml of cold water and once with 500 ml of cold water/ethanol (4/1), and dried at 50° C. and 100 mbar under a gentle nitrogen stream till dry. Yield about 99%.

Example 1e

Preparation of 7-amino-2(3H)-benzoxazolone 107.5 g (1 mole) of 5-chloro-7-nitro-2(3H)-benzoxazolone prepared according to Example 1d was suspended in 1000 ml of ethanol. 9.25 g of Pd/C 5% and 50 ml of ethanol were added and the mixture was hydrogenated at 4 bar hydrogen pressure for four to six hours at 60-65° C. while vigorously stirring. When the hydrogenation was complete, the mixture was cooled to 45° C. and filtered over Hyflo®. The Hyflo® was washed twice with 175 ml of methanol. 500 ml of solvent was distilled off under reduced pressure at 50° C., followed by addition of 250 ml of water and removal of 300 ml of solvent was by distillation under reduced pressure at 50° C. The last procedure was repeated twice and finally 250 ml of water was added and 400 ml of solvent was distilled off. The resulting mixture was cooled to 0-5° C. in about one hour. The solid was filtered off, washed three times with 125 ml of cold water, and dried at 50° C. and 100 mbar under a gentle nitrogen stream till dry. Yield about 94%.

Example 1f

Preparation of 3-[[bis(2-hydroxyethyl)amino]methyl]-1,1'-biphenyl

A mixture was prepared of 123.4 g of diethanolamine, 100 ml of water and 100 ml of methylethylketone (MEK) and 500 ml of methyl t-butyl ether while stirring under a mild nitrogen purge 124.75 g of. 3-(bromomethyl)-1,1'-biphenyl was added together with 750 ml of methyl t-butyl ether. The mixture was heated to reflux and refluxed for 18 hours, followed by cooling till room temperature. Thereafter the mixture was washed once with 375 ml of 2N NaOH and four times with 375 ml of water. The combined 2N NaOH and water layers were extracted with 750 ml of methyl t-butyl ether. The combined methyl t-butyl ether layers were washed with 250 ml of water followed by distillation of as much methyl t-butyl ether as possible from the organic layer. 1350 ml of methylethylketone was added and 600 ml of solvent was distilled of at atmospheric pressure. The solution was cooled to room temperature and stored for use in the next step. Yield based on quantitative assay 97%.

Example 1g

Preparation of Bifeprunox Mesylate (Crude)

A solution of 128.9 g of 3-[[bis(2-hydroxyethyl)amino] methyl]-1,1'-biphenyl in approximately 750 ml of methylethylketone prepared according to Example 1f was stirred under mild nitrogen purge. In a separate vessel 202 g of methanesulfonic anhydride was dissolved in 600 ml of methylethylketone at 10-20° C. To the solution of 3-[[bis(2-hydroxyethyl) amino]methyl]-1,1'-biphenyl in methylethylketone 212.8 g of triethylamine was added and 60 ml of methylethylketone. The solution of methanesulfonic anhydride was added in about 45-60 minutes to the 3-[[bis(2-hydroxyethyl)amino] methyl]-1,1'-biphenyl/triethylamine solution, while maintaining the temperature below 10° C. 60 ml of methylethylketone was added and the mixture was stirred for another 15 minutes, followed by drop wise addition of 109.7 g of methanesulfonic acid and addition of 60 ml of methylethylketone in order to rinse the addition vessel.

71.3 g of 7-amino-2(3H)-benzoxazolone, prepared according to Example 1e was suspended in 100 ml of methylethylketone and added to the reaction mixture followed by 60 ml of methylethylketone. The reaction mixture was heated to reflux and refluxed for 20-24 hours. After 20-24 hours of reflux 48 ml of water was added and the mixture was refluxed again for 1 hour. 420 ml of methylethylketone was added and 490 ml of methylethylketone/water was distilled of. This last step was repeated three times. 46.1 g of methanesulphonic acid was added, the mixture was refluxed for an additional hour and cooled down to room temperature in 1 hour. The mixture was further cooled down to 0-5° C. and stirred at this temperature for another hour. The solid was filtered off and, washed twice with 75 ml of cold methylethylketone, and dried at 50° C. and 100 mbar under a gentle nitrogen stream till dry. Yield about 76%.

Example 2

Preparation of Polymorphic Form α of Bifeprunox Mesylate in 2-propanol 10.06 g of bifeprunox mesylate crude prepared as described Example 1 g was suspended in a mixture of 200 ml of 2-propanol and 40 ml of water under nitrogen purge. The suspension was heated until reflux and cooled down to room temperature in 120 minutes under stirring. The formed suspension was further cooled down under stirring to 0° C. and stirred at this temperature for a further 120 minutes. The crystals were filtered of and dried at 50° C. and 100 mbar.

Example 3

Preparation of Polymorphic Form α of Bifeprunox Mesylate in Acetonitrile 50 g of bifeprunox mesylate prepared crude as described in Example 1g was suspended in a mixture of 875 ml of acetonitrile and 250 ml of water under nitrogen purge. 375 ml of acetonitrile was added and the reaction mixture was heated till reflux. 500 ml of solvent was distilled off and 500 ml of acetonitrile were added and this procedure was repeated for a second time. After distilling another 500 ml of solvent the mixture was cooled down to room temperature in 120 minutes. The mixture was further cooled down to 0-5° C. and stirred for 120 minutes at this temperature. The formed crystals were filtered off and washed twice with acetonitrile. The isolated crystals were dried at 50° C. and 100 mbar under a mild nitrogen purge. Yield 85.6%.

Example 4

Preparation of Polymorphic Form γ of Bifeprunox Mesylate

To a suspension of 12.50 g of bifeprunox mesylate (crude) prepared as described in Example 1g in 150 ml of methylethylketone (MEK) 75 ml of a 5% NaHCO$_3$ solution was added in about 10-15 min. After 5-10 minutes of stirring the suspension was filtered over Hyflo® or Celite® into another vessel where the layers were separated. The water layer was extracted with 125 and 75 ml of methylethylketone. The methylethylketone layers were combined and washed with a mixture of 50 ml of water and 10 ml of ethanol 96%.

The methylethylketone layer was filtered through a 1 μm filter into a clean vessel, after which the filter was rinsed with 25 ml of methylethylketone. Methylethylketone was distilled off until a volume of about 130 ml was reached, 200 ml of methylethylketone was added and again methylethylketone was distilled off to reach a volume of 175 ml.

Next, a solution of 3.00 grams of methane sulphonic acid in 50 ml of methylethylketone was added in about 30 min. After cooling to 5° C. and stirring for 1½ hours at this temperature the product was filtered off and washed twice with 50 ml of cold methylethylketone. After drying at 50° C. and 100 mbar under a mild nitrogen purge the gamma (γ) polymorph of bifeprunox mesylate yield was about 80%.

Example 5

Preparation of a 10 mg Capsule Formulation of Polymorphic Form α of Bifeprunox Mesylate 2.227 kg of lactose was sieved and filled into a high shear mixer. 125 g of bifeprunox mesylate in its polymorphic form α was sieved and added. The composition was mixed with a high shear mixer (e.g. Collette Gral 10 or Collette Gral 75) until it was homogenous (approximately 4 minutes). 24 g of a disintegrant (e.g. sodium starch glycolate USP-NF such as Primojel®) and 24 g of a lubricant (e.g. sodium stearyl fumarate such as PRUV®) were added and the composition was mixed again until it was homogenous (approximately 1 minute). The powder was filled into capsules size 0, 240 mg per capsule by means of a capsule filling machine (e.g. Zanasi LZ 64 or Zanasi RM63 plug filler). Approximately 10,000 filled capsules were obtained.

Example 6

Preparation of a 10 mg Tablet Formulation of Bifeprunox Mesylate Polymorphic Form α

Tablets with a strength of 10 mg were prepared according to the following procedures (required quantities are given in Table 8). One third of the given amount of lactose monohydrate was sieved and filled into a high shear mixer and mixed during 5 minutes. The required amount of milled bifeprunox mesylate in its polymorphic form α was added to the mixture, together with 0.100 kg sodium starch glycolate, type A, 2.32 kg microcrystalline cellulose and the remainder of the lactose monohydrate. The composition was mixed with a high shear mixer (e.g. Collette Gral 10 or Collette Gral 75) until it was homogenous (approximately 10 minutes). The required amount of a sodium stearyl fumarate (such as PRUV®), sieved through a 0.42 mm sieve was added and the composition was mixed again until it was homogenous (approximately 5 minutes). The final product was compressed with 300 MPa into tablets. The product was coated using 15% m/m of the indicated Opadry II HP water suspension to 3.5% of the core weight.

Table 8 shows the amount of active ingredient and auxiliary materials used in a large scale production of 10 mg bifeprunox mesylate tablets.

TABLE 8

| Components | Per batch of 83333 10 mg tablets (in kg) |
|---|---|
| Core components | |
| Bifeprunox mesylate (milled) | 1.041 |
| Lactose monohydrate | 16.33 |
| Microcrystalline cellulose | 2.32 |
| Sodium starch glycolate, type A | 0.100 |
| Sodium stearyl fumarate | 0.200 |
| Coating components | |
| Opadry II HP beige 85F27126 | 0.700 |
| Purified water | 3.968 |

Example 7

Analytical Methods

XRPD patterns were measured on a diffractometer using monochromatic CuKα radiation (tube voltage 40 kV, tube current 40 mA) at room temperature. IR spectra were recorded on a Fourier transform IR spectrometer in attenuated total reflectance (silicon crystal) with a spectral resolution of 2 $cm^{-1}$ using a mercury cadmium telluride detector.

Melting points were determined on a DSC apparatus as onset temperatures of the melting endotherm using 40 μL aluminum crucibles with a pierced lid. Temperature program: heating from 25° C. up to 300° C. with 10 K $min^{-1}$. $N_2$ atmosphere at a flow of 80 mL $min^{-1}$.

The solid state $^{13}C$ NMR spectra were obtained using the cross-polarisation magic-angle spinning (CP/MAS) accessory on a Bruker AM300 instrument (contact time of 4 ms, recycle delay 3 s, spectral width 30 kHz, $^1H$ 90° pulse of 6 μs, spinning rate about 8.5 kHz. A standard 4 mm Bruker CP/MAS probe was used. Chemical shifts are referred to glycine ($\delta_c$=176.03 ppm for the C=O resonance).

Crystals of the alpha (α) form appeared under the microscope as block-shaped, those of the gamma (γ) crystal form were plate- or rod-shaped, whereas crystals of the delta (δ) crystal form looked block-shaped with rounded edges.

For each crystal form, a crystal was transferred into the cold nitrogen stream on a rotating anode X-ray diffractometer. The structures were solved by automated direct methods. Hydrogen atoms bonded to nitrogen were located on an electron-density map and their coordinates were included as parameters in the refinement. Other hydrogen atoms were included in the refinement on calculated positions riding on their carrier atoms. All non-hydrogen atoms were refined with anisotropic atomic displacement parameters. Hydrogen atoms were given fixed displacement factors, related to those of their carrier atoms.

Example 8

Pharmacokinetic Study

A single center, open label, randomized, double two-way cross-over study was used to assess the relative bioavailability of a 0.125 mg and a 20 mg (active ingredient amount) capsule formulation (δ polymorphic form of bifeprunox mesylate) respectively with a 0.125 mg and 20 mg (active ingredient amount) tablet formulation of the a polymorphic form of bifeprunox mesylate after oral administration to healthy male and female volunteers. Capsules and tablets were prepared substantially as described in Examples 5 and 6 with appropriate adjustments for dose and formulation, e.g., capsules or tablets.

Treatment started with a single dose of 0.125 mg bifeprunox mesylate as either a capsule or tablet formulation. The first cross-over started on Day 3 when a single dose of 0.125 mg bifeprunox mesylate, in the opposite formulation than that started with, was given. Next, after one drug free day, the subjects were uptitrated with the Day 3 formulation over a period of 8 days (Days 5-12). Subsequently, the 20 mg formulation was given for an additional 3 days (Days 13-15), followed by a second cross-over to a 20 mg treatment of the first formulation (capsule or tablet) for four days (Days 16-19).

Pharmacokinetic parameters were determined two times for 48 hours starting on Days 1 and 3 (for the single dose pharmacokinetics), and two times for 24 hours starting on Days 15 and 19 (for multiple dose pharmacokinetics). For differences between the test (tablet) and the reference (capsule) treatment, 90% confidence intervals are given for the 0.125 mg and 20 mg treatments. The information for the 0.125 data is extracted out of the Day 1 and Day 3 measurements, while the steady state plasma levels of Day 15 and Day 19 are used for the pharmacokinetic information of the 20 mg regimen.

Pharmacokinetic results are shown in Table 9.

TABLE 9

| Dose (mg) | Formulation | $T_{max}$ (hr) | $C_{max}$ (ng/ml) | $AUC_{0-t}$ (hr · ng/ml) | $AUC_{0-24}$ (hr · ng/ml) | AUC (hr · ng/ml) |
|---|---|---|---|---|---|---|
| 0.125 | Capsule (δ) | 3.16 | 0.155 | 0.904 | — | 1.31 |
| 0.125 | Tablet (α) | 2.31 | 0.281 | 1.46 | — | 1.69 |
| 20 | Capsule (δ) | 2.00 | 50.8 | — | 352 | — |
| 20 | Tablet (α) | 1.81 | 54.1 | — | 349 | — |

As is shown above, the bioavalability (AUC, $C_{max}$) of the 0.125 mg tablet was higher compared to the reference capsule. Compared to the capsule, that tablet also exhibited a faster $T_{max}$. From 6 hours post administration up to the last measurable plasma concentrations, the average plasma concentration time profiles were nearly congruent for both formulations.

Following multiple 20 mg doses, no major differences were found between the capsule and tablet formulation. For the AUC, the 90% confidence intervals of the ratio tablet/capsule were within the 80%-125% range.

Example 9

Tablet Dissolution

Three different strengths of tablets (10 mg, 5 mg and 1 mg of bifeprunox mesylate) were prepared having the compositions shown in Table 10; the tablets were designated T1, T2 and T3, respectively.

TABLE 10

|  | T1 | T2 | T3 |
|---|---|---|---|
| Label claim, mg/tablet | 10.0 | 5.0 | 1.0 |
| Component | Quantity (mg) | | |
| Bifeprunox | 12.49 | 6.25 | 1.25 |
| Lactose monohydrate | 3.75 | 4.50 | 3.60 |
| Lactose monohydrate[1] | 106.26 | 136.25 | 112.75 |
| Sodium starch glycolate | 1.25 | 1.50 | 1.20 |
| Sodium stearyl fumarate | 1.25 | 1.50 | 1.20 |

[1]Direct Compression

Each of the tablets were placed in a dissolution test under the following conditions: Apparatus: paddle method; Stirring speed: 50 rpm; Amount of test dissolution medium: 900 ml; Temperature of dissolution medium: 37° C.±0.5° C.

Six different dissolution media were used as follows:

Media 1: Dissolve 2.0 g of sodium chloride dissolved in 7.0 ml of hydrochloric acid, q.s. with water to make 1000 ml (pH 1.2);

Media 2: McIlvaine buffer solution (pH 3.0), pH adjusted with 0.05 mol/L of sodium hydrogen phosphate and 0.025 mol/L of citric acid;

Media 3: McIlvaine buffer solution (pH 4.0);

Media 4: McIlvaine buffer solution (pH 5.0);

Media 5: Water;

Media 6: To 250 ml of 0.2 mol/L potassium dihydrogenphosphate TS add 118 ml of 0.2 mol/L sodium hydroxide TS and water to make 1000 ml.

Tables 11-16 show dissolution results in each of the above media, respectively. Dissolution testing was performed in triplicate.

TABLE 11

| | Media 1 | | | | | | | | |
|---|---|---|---|---|---|---|---|---|---|
| | 10 × 1.0 mg tablets % RLC dissolved bifeprunox | | | 2 × 5.0 mg tablets % RLC dissolved bifeprunox | | | 1 × 10.0 mg tablets % RLC dissolved bifeprunox | | |
| Time in minutes | Vessel 1 | Vessel 2 | Vessel 3 | Vessel 1 | Vessel 2 | Vessel 3 | Vessel 1 | Vessel 2 | Vessel 3 |
| 0 | <LOD | <LOD | <LOD | <LOD | <LOD | <LOD | <LOD | <LOD | <LOD |
| 60 | 24.1 | 24.4 | 23.7 | 24.0 | 22.5 | 14.6 | 14.0 | 13.1 | 1.5 |
| 120 | 26.1 | 26.5 | 25.9 | 26.3 | 24.9 | 18.2 | 17.6 | 16.7 | 1.8 |
| 180 | 27.1 | 27.5 | 27.1 | 27.5 | 26.2 | 20.1 | 19.6 | 18.8 | 2.1 |
| 240 | 27.9 | 28.1 | 27.9 | 28.4 | 27.0 | 21.5 | 20.9 | 20.2 | 2.3 |
| 300 | 28.4 | 28.7 | 28.4 | 28.9 | 27.4 | 22.4 | 21.9 | 21.3 | 2.5 |

TABLE 12

Media 2

| Time in minutes | 10 × 1.0 mg tablets % RLC dissolved bifeprunox | | | 2 × 5.0 mg tablets % RLC dissolved bifeprunox | | | 1 × 10.0 mg tablets % RLC dissolved bifeprunox | | |
| --- | --- | --- | --- | --- | --- | --- | --- | --- | --- |
| | Vessel 1 | Vessel 2 | Vessel 3 | Vessel 1 | Vessel 2 | Vessel 3 | Vessel 1 | Vessel 2 | Vessel 3 |
| 0 | <LOD | <LOD | <LOD | <LOD | <LOD | <LOD | <LOD | <LOD | <LOD |
| 6 | 68.7 | 70.4 | 78.2 | 70.2 | 69.0 | 78.7 | 99.3 | 96.4 | 94.9 |
| 12 | 95.3 | 91.6 | 94.6 | 93.6 | 92.9 | 94.5 | 103.6 | 102.0 | 102.8 |
| 20 | 99.2 | 97.1 | 97.4 | 97.8 | 99.6 | 97.9 | 106.5 | 104.8 | 103.2 |
| 30 | 100.3 | 97.7 | 98.5 | 99.6 | 101.6 | 98.0 | 106.1 | 105.5 | 104.1 |
| 45 | 101.1 | 99.1 | 97.9 | 100.3 | 102.5 | 98.2 | 107.6 | 107.3 | 104.3 |
| 60 | 100.9 | 100.2 | 99.2 | 99.8 | 102.6 | 98.7 | 107.0 | 106.7 | 104.7 |

TABLE 13

Media 3

| Time in minutes | 10 × 1.0 mg tablets % RLC dissolved bifeprunox | | | 2 × 5.0 mg tablets % RLC dissolved bifeprunox | | | 1 × 10.0 mg tablets % RLC dissolved bifeprunox | | |
| --- | --- | --- | --- | --- | --- | --- | --- | --- | --- |
| | Vessel 1 | Vessel 2 | Vessel 3 | Vessel 1 | Vessel 2 | Vessel 3 | Vessel 1 | Vessel 2 | Vessel 3 |
| 0 | 0.2 | 0.2 | 0.2 | 0.2 | 0.2 | 0.2 | 0.2 | 0.2 | 0.2 |
| 6 | 59.9 | 58.8 | 65.0 | 33.9 | 36.2 | 33.1 | 47.1 | 52.0 | 57.7 |
| 12 | 80.2 | 79.8 | 84.6 | 50.5 | 50.6 | 50.3 | 67.7 | 69.6 | 79.0 |
| 20 | 90.1 | 92.9 | 91.0 | 67.0 | 64.2 | 66.5 | 89.4 | 82.5 | 84.1 |
| 30 | 92.3 | 96.5 | 93.1 | 75.1 | 74.8 | 74.1 | 91.3 | 90.4 | 89.8 |
| 45 | 95.2 | 98.8 | 95.1 | 82.6 | 82.4 | 82.9 | 97.4 | 94.8 | 96.0 |
| 60 | 96.5 | 98.9 | 94.9 | 86.4 | 86.5 | 86.8 | 97.1 | 96.5 | 96.6 |

TABLE 14

Media 4

| Time in minutes | 10 × 1.0 mg tablets % RLC dissolved bifeprunox | | | 2 × 5.0 mg tablets % RLC dissolved bifeprunox | | | 1 × 10.0 mg tablets % RLC dissolved bifeprunox | | |
| --- | --- | --- | --- | --- | --- | --- | --- | --- | --- |
| | Vessel 1 | Vessel 2 | Vessel 3 | Vessel 1 | Vessel 2 | Vessel 3 | Vessel 1 | Vessel 2 | Vessel 3 |
| 0 | <LOD | <LOD | <LOD | <LOD | <LOD | <LOD | <LOD | <LOD | <LOD |
| 60 | 34.9 | 38.0 | 34.4 | 41.7 | 32.6 | 37.6 | 35.6 | 22.6 | 25.4 |
| 120 | 46.5 | 34.1 | 47.4 | 46.9 | 43.6 | 38.5 | 41.0 | 41.6 | 37.0 |
| 180 | 39.6 | 39.4 | 45.8 | 33.4 | 44.1 | 41.1 | 39.2 | 43.5 | 34.2 |
| 240 | 38.8 | 45.5 | 43.0 | 45.6 | 50.8 | 49.0 | 44.0 | 50.9 | 36.9 |
| 300 | 47.1 | 34.0 | 40.5 | 57.1 | 42.3 | 37.1 | 53.7 | 50.6 | 58.1 |

TABLE 15

Media 5

| Time in minutes | 10 × 1.0 mg tablets % RLC dissolved bifeprunox | | | 2 × 5.0 mg tablets % RLC dissolved bifeprunox | | | 1 × 10.0 mg tablets % RLC dissolved bifeprunox | | |
| --- | --- | --- | --- | --- | --- | --- | --- | --- | --- |
| | Vessel 1 | Vessel 2 | Vessel 3 | Vessel 1 | Vessel 2 | Vessel 3 | Vessel 1 | Vessel 2 | Vessel 3 |
| 0 | <LOD | <LOD | <LOD | <LOD | <LOD | <LOD | <LOD | <LOD | <LOD |
| 6 | 65.3 | 64.9 | 71.6 | 73.6 | 72.3 | 60.4 | 70.8 | 84.9 | 77.1 |
| 12 | 82.8 | 88.5 | 91.0 | 86.7 | 86.4 | 87.9 | 92.7 | 89.5 | 96.8 |
| 20 | 89.9 | 95.9 | 96.0 | 91.1 | 90.2 | 94.7 | 97.1 | 97.8 | 102.2 |
| 30 | 91.3 | 97.0 | 97.2 | 92.5 | 91.2 | 97.1 | 100.4 | 98.6 | 105.7 |
| 45 | 92.0 | 97.8 | 97.7 | 93.0 | 91.2 | 98.7 | 101.6 | 100.5 | 106.4 |
| 60 | 91.9 | 98.0 | 97.8 | 92.7 | 91.1 | 99.6 | 102.5 | 101.1 | 107.8 |

TABLE 16

| | Media 6 | | | | | | | | |
|---|---|---|---|---|---|---|---|---|---|
| | 10 × 1.0 mg tablets % RLC dissolved bifeprunox | | | 2 × 5.0 mg tablets % RLC dissolved bifeprunox | | | 1 × 10.0 mg tablets % RLC dissolved bifeprunox | | |
| Time in minutes | Vessel 1 | Vessel 2 | Vessel 3 | Vessel 1 | Vessel 2 | Vessel 3 | Vessel 1 | Vessel 2 | Vessel 3 |
| 0 | <LOD | <LOD | <LOD | <LOD | <LOD | <LOD | <LOD | <LOD | <LOD |
| 60 | 6.9 | 8.2 | 7.9 | 7.1 | 4.1 | <LOD | <LOD | <LOD | <LOD |
| 120 | 6.6 | 8.3 | 7.2 | 7.7 | 5.4 | <LOD | <LOD | <LOD | <LOD |
| 180 | 7.1 | 10.3 | 7.5 | 7.6 | 5.2 | <LOD | <LOD | <LOD | <LOD |
| 240 | 9.9 | 9.2 | 7.8 | 8.0 | 7.3 | <LOD | <LOD | <LOD | <LOD |
| 300 | 7.5 | 9.1 | 8.0 | 8.3 | 7.6 | <LOD | <LOD | <LOD | <LOD |

As can be seen in the above tables, there is no difference in dissolution behavior between 1.0 mg, 5.0 mg and 10.0 mg tablets of bifeprunox. Bifeprunox dissolves almost immediately in McILvaine buffer pH 3.0.

It is believed that the difference in dissolved bifeprunox in Table 11 between 1.0 mg, 5.0 mg and 10.0 mg tablets is caused by the different amounts of excipients, e.g. 10 tablets of 1.0 mg, 2 tablets of 5.0 mg and 1 tablet of 10.0 mg in the dissolution vessels. Some of the excipients are surface active.

Overall, the dissolution behavior of tablets with the strengths of 1.0 mg, 5.0 mg and 10.0 mg bifeprunox are substantially the same.

What is claimed is:

1. A pharmaceutical composition comprising an effective amount of an active ingredient comprising a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
   wherein, following administration of an effective amount of the composition to a human subject, the subject exhibits at least one of:
   (a) a plasma $T_{max}$ of 7-[4-([1,1'-biphenyl]-3-ylmethyl)-1-piperazinyl]-2(3H)-benzoxazolone within at most about 3 hours;
   (b) a plasma $C_{max}$ of 7-[4-([1,1'-biphenyl]-3-ylmethyl)-1-piperazinyl]-2(3H)-benzoxazolone of at least about 0.1 ng/ml; or
   (c) a plasma $AUC_{0-24}$ of 7-[4-([1,1'-biphenyl]-3ylmethyl)-1-piperazinyl]-2(3H)-benzoxazolone of at least about 0.9 hr·ng/ml.

2. A pharmaceutical composition comprising an effective amount of an active ingredient comprising a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
   wherein the crystalline polymorph exhibits an X-ray powder diffraction pattern having characteristic peaks expressed in degrees 2 θ at approximately 7.0, 9.3, 10.0, 12.5, 15.4, 16.7, 17.2, 17.4, 17.7, 18.7, 21.3, 22.2, 25.2, 27.2, 28.3, 28.8 and 30.1, and
   wherein, following administration of an effective amount of the composition to a human subject, the subject exhibits at least one of:
   (a) a plasma $T_{max}$ of 7-[4-([1,1'-biphenyl]-3-ylmethyl)-1-piperazinyl]-2(3H)-benzoxazolone within at most about 3 hours;
   (b) a plasma $C_{max}$ of 7-[4-([1,1'-biphenyl]-3-ylmethyl)-1-piperazinyl]-2(3H)-benzoxazolone of at least about 0.1 ng/ml; or
   (c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

3. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
   wherein the crystalline polymorph has a melting point at approximately 277° C., and
   wherein, following administration of an effective amount of the composition to a human subject, the subject exhibits at least one of:
   (a) a plasma $T_{max}$ of 7-[4-([1,1'-biphenyl]-3-ylmethyl)-1-piperazinyl]-2(3H)-benzoxazolone within at most about 3 hours;
   (b) a plasma $C_{max}$ of 7-[4-([1,1'-biphenyl]-3-ylmethyl)-1-piperazinyl]-2(3H)-benzoxazolone of at least about 0.1 ng/ml; or
   (c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

4. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
   wherein the crystalline polymorph exhibits a complete DSC trace substantially as shown in FIG. 2, and
   wherein, following administration of an effective amount of the composition to a human subject, the subject exhibits at least one of:
   (a) a plasma $T_{max}$ of 7-[4-([1,1'-biphenyl]-3-ylmethyl)-1-piperazinyl]-2(3H)-benzoxazolone within at most about 3 hours;
   (b) a plasma $C_{max}$ of 7-[4-([1,1'-biphenyl]-3-ylmethyl)-1-piperazinyl]-2(3H)-benzoxazolone of at least about 0.1 ng/ml; or
   (c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

5. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
   wherein the crystalline polymorph exhibits an attenuated total reflectance infrared spectrum having characteristic absorption bands expressed in reciprocal centimeters at approximately 1764, 1217, 795, 746 and 694, and wherein, following administration of an effective amount of the composition to a human subject, the subject exhibits at least one of:
(a) a plasma $T_{max}$ of 7-[4-([1,1'-biphenyl]-3-ylmethyl)-1-piperazinyl]-2(3H)-benzoxazolone within at most about 3 hours;
(b) a plasma $C_{max}$ of 7-[4-([1,1'-biphenyl]-3-ylmethyl)-1-piperazinyl]-2(3H)-benzoxazolone of at least about 0.1 ng/ml; or
(c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

6. A pharmaceutical composition according to claim 5, wherein the crystalline polymorph exhibits an attenuated total reflectance infrared spectrum having characteristic absorption bands expressed in reciprocal centimeters at approximately 1764, 1636, 1284, 1217, 809, 795, 746, 694, 663 and 509.

7. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits a complete IR spectrum substantially as shown in FIG. 3, and
wherein, following administration of an effective amount of the composition to a human subject, the subject exhibits at least one of:
(a) a plasma $T_{max}$ of 7-[4-([1,1'-biphenyl]-3-ylmethyl)-1-piperazinyl]-2(3H)-benzoxazolone within at most about 3 hours;
(b) a plasma $C_{max}$ of 7-[4-([1,1'-biphenyl]-3-ylmethyl)-1-piperazinyl]-2(3H)-benzoxazolone of at least about 0.1 ng/ml; or
(c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

8. A pharmaceutical composition comprising an effective amount of a crystalline polymorph of 7-[4-([1,1'-biphenyl]-3-ylmethyl)-1-piperazinyl]-2(3H)-benzoxazolone monomethanesuIfonate and at least one pharmaceutically acceptable excipient,
wherein the crystalline polymorph exhibits $^{130}C$ solid state NMR chemical shifts expressed relative to glycine ($\delta_c$=176.03 for the C=O resonance) at approximately 40.4, 48.7, 56.5, 106.8 and 137.7 ppm, and
wherein, following administration of an effective amount of the composition to a human subject, the subject exhibits at least one of:
(a) a plasma $T_{max}$ of 7-[4-([1,1'-biphenyl]-3-ylmethyl)-1-piperazinyl]-2(3H)-benzoxazolone within at most about 3 hours;
(b) a plasma $C_{max}$ of 7-[4-([1,1 -biphenyl]-3-ylmethyl)-1-piperazinyl]-2(3H)-benzoxazolone of at least about 0.1 ng/ml; or
(c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

9. A pharmaceutical composition according to claim 8, wherein the crystalline polymorph exhibits $^{13}C$ solid state NMR chemical shifts expressed relative to glycine ($\delta_c$=176.03 for the C=O resonance) at approximately 40.4, 48.7, 50.3, 56.5, 106.8, 110.7, 124.9, 126.9, 127.8, 129.2, 130.8, 134.2, 137.7, 141.6, and 153.8 ppm.

Figure 4:
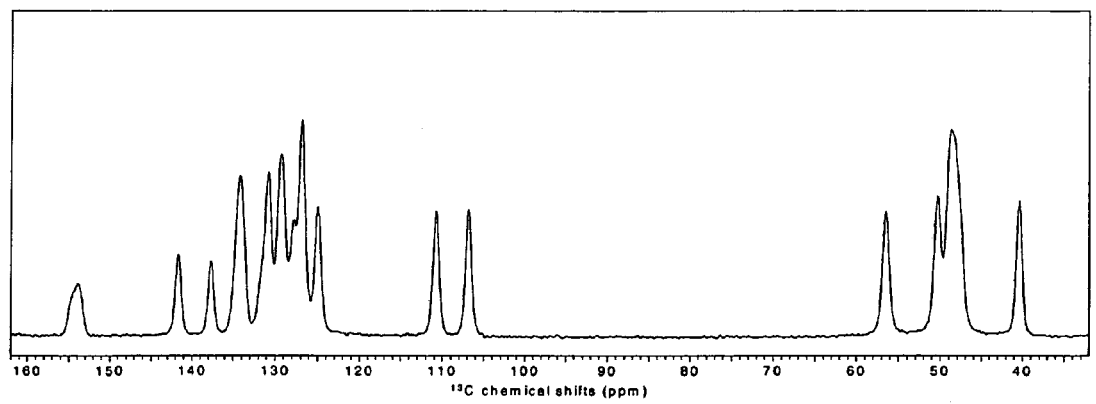
FIG. 4 shows a $^{13}C$ solid state NMR spectrum of polymorphic form a of bifeprunox mesylate.

10. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits $^{130}C$ solid state NMR chemical shifts relative to glycine ($\delta_c$=176.03 for the C=O resonance) substantially as shown in FIG. 4, and
wherein, following administration of an effective amount of the composition to a human subject, the subject exhibits at least one of:
(a) a plasma $T_{max}$ of 7-[4-([1,1'-biphenyl]-3-ylmethyl)-1-piperazinyl]-2(3H)-benzoxazolone within at most about 3 hours;
(b) a plasma $C_{max}$ of 7-[4-([1,1'-biphenyl]-3-ylmethyl)-1-piperazinyl]-2(3H)-benzoxazolone of at least about 0.1 ng/ml; or
(c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

11. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits a single crystal X-ray crystallographic analysis at 150K having
(a) crystal parameters that are approximately equal to the following:

| Cell dimensions | a = 9.823 Å |
| --- | --- |
| | b = 10.737 Å |
| | c = 12.690 Å |
| | α = 98.553° |
| | β = 93.749° |
| | γ = 116.097° |
| Crystal system | triclinic |
| Space group | P-1 |
| Molecules/unit cell | 2 |
| Density (g/cm³) | 1.481 | and (b) corresponding atomic positions of all atoms relative to the origin of the unit cell,
wherein, following administration of an effective amount of the composition to a human subject, the subject exhibits at least one of:
(a) a plasma $T_{max}$ of 7-[4-([1,1'-biphenyl]-3-ylmethyl)-1-piperazinyl]-2(3H)-benzoxazolone within at most about 3 hours;
(b) a plasma $C_{max}$ of 7-[4-([1,1'-biphenyl]-3-ylmethyl)-1-piperazinyl]-2(3H)-benzoxazolone of at least about 0.1 ng/ml; or
(c) a plasma $AUC_{0-24}$ of 7-[4-([1,1'-biphenyl]-3-ylmethyl)-1-piperazinyl]-2(3H)-benzoxazolone of at least about 0.9 hr·ng/ml.

12. A pharmaceutical composition comprising a therapeutically effective amount of an active compound and at least one pharmaceutically acceptable excipient,
wherein the active compound comprises 7-[4-([1,1'-biphenyl]-3-ylmethyl)-1-piperazinyl]-2(3H)-benzoxazolone monomethanesulfonate,
wherein at least about 50% by weight of the active compound is crystalline polymorphic form α, and
wherein, following administration of an effective amount of the composition to a human subject, the subject exhibits at least one of:

(a) a plasma T$_{max}$ of 7-[4-([1,1'-biphenyl]-3-ylmethyl)-1-piperazinyl]-2(3H)-benzoxazolone within at most about 3 hours;

(b) a plasma C$_{max}$ of 7-[4-([1,1'-biphenyl]-3-ylmethyl)-1-piperazinyl]-2(3H)-benzoxazolone of at feast about 0.1 ng/ml; or (c) a plasma AUC$_{0-24}$ of 7-[4-([1,1'-biphenyl]-3-ylmethyl)-1-piperazinyl]-2(3H)-benzoxazolone of at least about 0.9 hr·ng/ml.

13. A pharmaceutical composition according to claim 12, wherein at least about 60% by weight of the active compound is crystalline polymorphic form α.

14. A pharmaceutical composition according to claim 13, wherein at least about 80% by weight of the active compound is crystalline polymorphic form α.

15. A pharmaceutical composition according to claim 14, wherein at least about 90% by weight of the active compound is crystalline polymorphic form α.

16. A pharmaceutical composition according to claim 15, wherein at least about 95% by weight of the active compound is crystalline polymorphic form α.

17. A pharmaceutical composition according to claim 12, further comprising lactose monohydrate, microcrystalline cellulose, sodium starch glycolate type A and sodium stearyl fumarate.

18. A pharmaceutical composition according to claim 17, comprising about 70% to about 90% w/w of lactose monohydrate, about 10% to about 15% w/w of microcrystalline cellulose, about 0.3% to about 0.7% w/w of sodium starch glycolate type A, about 0.6% to about 1.3% w/w of sodium stearyl fumarate and about 0 to about 0.5% w/w colloidal anhydrous silica.

19. A method of treating a central nervous system (CNS) disorder in a human patient in need thereof, comprising administering to the patient a pharmaceutical composition comprising a crystalline polymorph of 7-[4-([1,1'-biphenyl]-3-ylmethyl)-1-piperazinyl]-2(3H)-benzoxazolone monomethanesulfonate in an amount effective for treatment of the disorder, wherein the effective amount of the crystalline polymorph administered to the patient results in exhibition of at least one of:

(a) a plasma T$_{max}$ of 7-[4-([1,1'-biphenyl]-3-ylmethyl)-1-piperazinyl]-2(3H)-benzoxazolone within at most about 3 hours;

(b) a plasma C$_{max}$ of 7-[4-([1,1'-biphenyl]-3-ylmethyl)-1-piperazinyl]-2(3H)-benzoxazolone of at least about 0.1 ng/ml; or (c) a plasma AUC$_{0-24}$ of 7-[4-([1,1'-biphenyl]-3-ylmethyl)-1-piperazinyl]-2(3H)-benzoxazolone of at least about 0.9 1.4 hr·ng/ml wherein the CNS disorder is chosen from schizophrenia, Parkinson's disease.

20. A method according to claim 19, wherein the crystalline polymorph comprises at least one polymorph chosen from crystalline polymorphic form α, crystalline polymorphic form γ, and crystalline polymorphic form δ.

21. A method of treating a central nervous system (CNS) disorder in a human patient in need thereof, comprising administering to the patient a pharmaceutical composition comprising a crystalline polymorph of 7-[4-([1,1-biphenyl]-3-ylmethyl)-1-piperazinyl]-2(3H)-benzoxazolone monomethanesuIfonate in an amount effective for treatment of the disorder, wherein the crystalline polymorph is crystalline polymorphic form α, and wherein the effective amount of the crystalline polymorph administered to the patient results in exhibition of at least one of:

(a) a plasma T$_{max}$ of 7-[4-([1,1'-biphenyl]-3-ylmethyl)-1-piperazinyl]-2(3H)-benzoxazolone within at most about 3 hours;

(b) a plasma C$_{max}$ of 7-[4-([1,1'-biphenyl]-3-ylmethyl)-1-piperazinyl]-2(3H)-benzoxazolone of at least about 0.1 ng/ml; or (c) a plasma AUC$_{0-24}$ of 7-[4-([1,1'-biphenyl]-3-ylmethyl)-1-piperazinyl]-2(3H)-benzoxazolone of at least about 0.9 1.4 hr·ng/ml wherein the CNS disorder is chosen from schizophrenia, Parkinson's disease.

22. A pharmaceutical composition comprising an effective amount of an active ingredient comprising bifeprunox mesylate chosen from α (alpha), δ (delta) and γ (gamma) polymorphic forms and at least one pharmaceutically acceptable excipient, wherein the effective amount of bifeprunox mesylate ranges from about 0.05 to about 40 mg.

23. The composition of claim 22, wherein the effective amount of bifeprunox mesylate ranges from about 0.75 to about 35 mg.

24. The composition of claim 22, wherein the effective amount of bifeprunox mesylate ranges from about 0.1 to about 30 mg.

25. The composition of claim 22, wherein the effective amount of bifeprunox mesylate ranges from about 0.125 to about 20 mg.

26. The composition of claim 22, wherein the effective amount of bifeprunox mesylate comprises 0.125 mg.

27. The composition of claim 22, wherein the effective amount of bifeprunox mesylate comprises 1 mg.

28. The composition of claim 22, wherein the effective amount of bifeprunox mesylate comprises 5 mg.

29. The composition of claim 22, wherein the effective amount of bifeprunox mesylate comprises 10 mg.

30. The composition of claim 22, wherein the effective amount of bifeprunox mesylate comprises 20 mg.

* * * * *